United States Patent [19]

Theodoridis

[11] Patent Number: 5,521,147
[45] Date of Patent: May 28, 1996

[54] 3-(BENZOFURAN-7-YL)-6-HALOALKYLURACILS

[75] Inventor: George Theodoridis, Princeton, N.J.

[73] Assignee: FMC Corporation, Philadelphia, Pa.

[21] Appl. No.: 382,820

[22] Filed: Feb. 3, 1995

Related U.S. Application Data

[63] Continuation-in-part of Ser. No. 107,471, Aug. 13, 1993, abandoned.

[51] Int. Cl.[6] .................. C07D 239/54; A01N 43/54
[52] U.S. Cl. .................. 504/243; 544/310; 544/312; 544/314; 544/230; 544/311
[58] Field of Search .................. 544/310, 312, 544/314, 230, 311; 504/243

[56] References Cited

U.S. PATENT DOCUMENTS 5,346,881   9/1994   Theodoridis ..................... 504/243

Primary Examiner—John M. Ford
Attorney, Agent, or Firm—H. Robinson Ertelt; Robert M. Kennedy

[57] ABSTRACT

Herbicidal 3-(benzofuran-7-yl)-6-haloalkyluracils of the formula

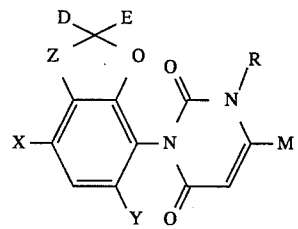

in which

M is fluoroalkyl $(C_{1-6})$; D is hydrogen, alkyl $(C_{1-6})$, or alkoxy$(C_{1-6})$-carbonyl; E is hydrogen or alkyl $(C_{1-6})$, or D and E taken together are —$CH_2CH_2$—; R is hydrogen, amino, alkyl $(C_{1-6})$, 2-alkenyl $(C_{3-6})$, 2-alkynyl $(C_{3-6})$, alkoxy$(C_{1-6})$methyl, benzyl, amino, fluoroalkyl $(C_{1-6})$, alkoxy $(C_{1-6})$-carbonylmethyl; or cyanoalkyl $(C_{1-6})$ having preferably one cyano group; X is hydrogen, fluorine, chlorine, bromine, cyano, alkyl$(C_{1-6})$, haloalkyl$(C_{1-6})$, haloalkoxy$(C_{1-6})$, or alkoxy$(C_{1-6})$; Y is hydrogen, alkyl $(C_{1-6})$, fluorine, chlorine, or bromine; and Z is $CH_2$, C=O, C=S, —CH(OH)—, —$CH_2CH_2$—, —CH=CH—, —(C=O)$CH_2$—; or C=N—O—R' wherein R' is alkyl$(C_{1-6})$.

24 Claims, No Drawings

3-(BENZOFURAN-7-YL)-6-HALOALKYLURACILS

This application is a continuation-in-part of application Ser. No. 08/107,471, filed Aug. 13, 1993, now abandoned.

This invention relates to uracil compounds which are useful as herbicides, and intermediates which are useful for producing herbicides. More particularly the present invention pertains to 3-(benzofuran-7-yl)-6-haloalkyluracils, methods of preparing them, their intermediates, their compositions, and methods of destroying unwanted plants by preemergence or postemergence application of the herbicidal compositions to the locus where control is desired. The herbicidal compounds of this invention may be used to effectively control a variety of grassy or broad leaf plant species.

One aspect of this invention relates to compounds of the formula

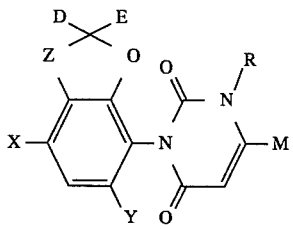

in which

M is fluoroalkyl ($C_{1-6}$, preferably $C_{1-3}$, more preferably $C_1$), having 1 to 6 fluorines;

D is hydrogen, alkyl ($C_{1-6}$, preferably $C_{1-3}$, more preferably $C_1$), or alkoxy($C_{1-6}$, preferably $C_{1-3}$)carbonyl;

E is hydrogen or alkyl ($C_{1-6}$, preferably $C_{1-3}$, more preferably $C_1$), or D and E taken together are —$CH_2CH_2$—;

R is hydrogen, amino, alkyl ($C_{1-6}$, preferably $C_{1-3}$, more preferably $C_1$), 2-alkenyl ($C_{3-6}$, preferably $C_{3-4}$, more preferably $C_3$), 2-alkynyl ($C_{3-6}$, preferably $C_{3-4}$, more preferably $C_3$), alkoxy ($C_{1-6}$, preferably $C_{1-3}$, more preferably $C_1$)methyl, benzyl, amino, fluoroalkyl ($C_{1-6}$, preferably $C_{1-3}$, more preferably $C_1$) having 1 to 6 fluorines, alkoxy ($C_{1-6}$, preferably $C_{1-3}$, more preferably $C_1$) carbonylmethyl; or cyanoalkyl ($C_{1-6}$, preferably $C_{1-3}$, more preferably $C_1$) having preferably one cyano group.

X is hydrogen, fluorine, chlorine, bromine, cyano, alkyl($C_{1-6}$, preferably $C_{1-3}$, more preferably $C_1$), haloalkyl($C_{1-6}$, preferably $C_{1-3}$, more preferably $C_1$), haloalkoxy($C_{1-6}$, preferably $C_{1-3}$, more preferably $C_1$), or alkoxy($C_{1-6}$, preferably $C_{1-3}$, more preferably $C_1$);

Y is hydrogen, alkyl ($C_{1-6}$, preferably $C_{1-3}$, more preferably $C_1$), fluorine, chlorine, or bromine; and Z is $CH_2$, C=O, C=S, —CH(OH)—, —$CH_2CH_2$—, —CH=CH—, —(C=O)$CH_2$—; or C=N—O—R' wherein R' is alkyl($C_{1-6}$, preferably $C_{1-3}$, more preferably $C_1$).

Haloalkyl and haloalkoxy substituents have 1 to 6 halogens which are independently fluorine, chlorine, and bromine. Preferably the haloalkyl and haloalkoxy substituents have 1 to 6 fluorines, the perfluoro $C_1$ and $C_2$ substituents are preferred.

Preferred compounds include those in which M is fluoromethyl or fluoroethyl; R is hydrogen, methyl, ethyl, or amino; E is hydrogen, methyl, or ethyl; D is methyl, ethyl, methoxycarbonyl, or ethoxycarbonyl; Z is $CH_2$, C=O, —CH(OH)—, —$CH_2CH_2$—, —CH=CH—, or —C=$NOCH_3$; and X and Y are independently hydrogen, fluorine, chlorine or bromine. More preferably M is trifluoromethyl or pentafluoroethyl; R is hydrogen, amino, or methyl; E is methyl or ethyl; D is methyl, ethyl, methoxycarbonyl, or ethoxycarbonyl; Z is $CH_2$, C=O, —CH(OH)—, —CH=CH—, or —C=$NOCH_3$; X is fluorine, bromine, or chlorine; and Y is hydrogen, fluorine, chlorine, or bromine. Still more preferably M is trifluoromethyl, R is methyl; E is methyl; D is methyl, methoxycarbonyl, or ethoxycarbonyl; Z is $CH_2$, C=O, —CH(OH)—, or —CH=CH—; X is fluorine, chlorine, or bromine; and Y is hydrogen, fluorine, chlorine or bromine.

Compounds that are particularly preferred include 3-(4-chloro-2,3-dihydro-2,2-dimethylbenzofuran-3-on-7-yl)-1-methyl-6-trifluoromethyluracil; 3-(4-fluoro-2,3-dihydro-2,2-dimethylbenzofuran-3-on-7-yl)-1-methyl-6-trfluoromethyluracil; 3-(4-bromo-2,3-dihydro-2,2-dimethylbenzofuran-3-on-7-yl)-1-methyl-6-trifluoromethyluracil; 3-(4-chloro-6-fluoro-2,3-dihydro-2,2-dimethylbenzofuran-3-on-7-yl)-1-methyl-6-trifluoromethyluracil; 3-(4,6-dichloro-2,3-dihydro-2,2-dimethylbenzofuran-3-on-7-yl)-1-methyl-6-trifluoromethyluracil; 3-(4-chloro-6-bromo-2,3-dihydro-2,2-dimethylbenzofuran-3-on-7-yl)-1-methyl-6-trifluoromethyluracil; 3-(4-fluoro-6-chloro-2,3-dihydro-2,2-dimethylbenzofuran-3-on-7-yl)-1-methyl-6-trifluoromethyluracil; 3-(4,6-difluoro-2,3-dihydro-2,2-dimethylbenzofuran-3-on-7-yl)-1-methyl-6-trifluoromethyluracil; 3-(4-chloro-6-fluoro-2,3-dihydro-2,2-dimethyl-3-hydroxybenzofuran-7-yl)-1-methyl-6-trifluoromethyluracil; 3-(5-chloro-2,2-dimethyl-7-fluoro-2H-1-benzopyran-8-yl)-1-methyl-6-trifluoromethyluracil; 3-(4-bromo-2,3-dihydro-2-methoxycarbonyl-2-methylbenzofuran-7-yl)-1-methyl-6-trifluoromethyluracil; 3-(4-bromo-2,3-dihydro-2-methoxycarbonyl-2-methylbenzofuran-3-on-7-yl)-1-methyl-6-trifluoromethyluracil; 1-amino-3-(4-chloro-2,3-dihydro-2,2-dimethylbenzofuran-3-on-7-yl)-6-trifluoromethyluracil, 3-(4-chloro-6-fluoro-2,3-dihydro-2,2-dimethyl-3-hydroxybenzofuran-7-yl)-1-methyl-6-trifluoromethyluracil; 3-(5-chloro-2,2-dimethyl-7-fluoro-2H-1-benzopyran-8-yl)-1-methyl-6-trifluoromethyluracil; 3-(4-bromo-2,3-dihydro-2-methoxycarbonyl-2-methylbenzofuran-7-yl )-1-methyl-6-trifluoromethyluracil; -(4-bromo-2,3-dihydro-2-methoxycarbonyl-2-methylbenzofuran-3-on-7-yl)-1-methyl-6-trifluoromethyluracil; and 1-amino-3-(4-chloro-2,3-dihydro-2,2-dimethylbenzofuran-3-on-7-yl)-6-trifluoromethyluracil.

Representative compounds of this invention are listed in Table 1 and Table 1a. Characterizing properties of various compounds are listed in Table 2.

Using commercially available starting materials or those whose synthesis is known in the art, the compounds of this invention may be prepared using methods described in the following Examples and schemata, or by using modifications thereof that are within the skill of the art.

Many of the compounds of this invention may be prepared according to the following reaction schemata.
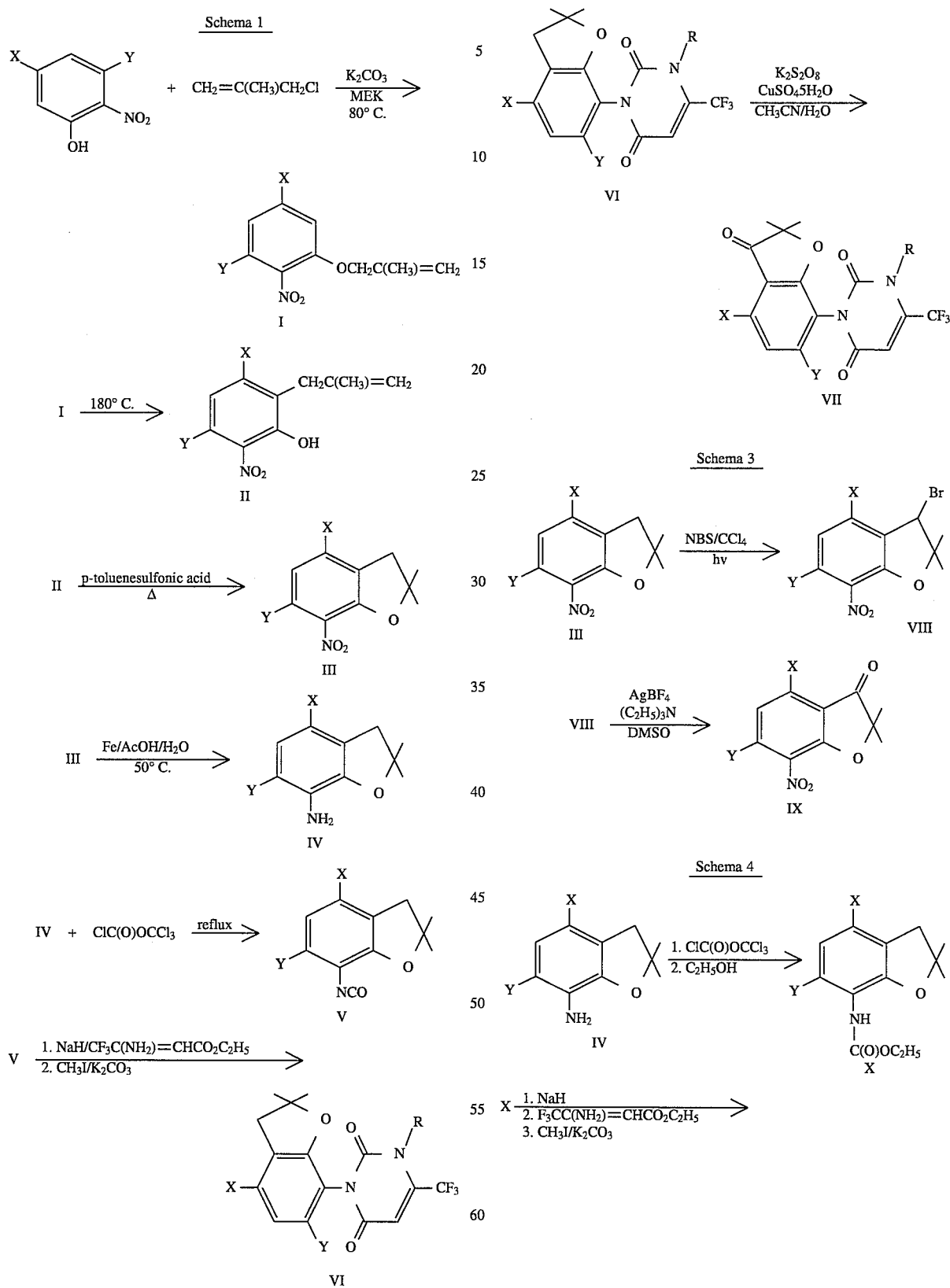

Schema 4 -continued

VI

Schema 5 where Y is F

XI

XI → XII (Jones Reagent)

XII → XIII (PCl₃/AlCl₃, CH₂Cl₂)

XIII → XIV (NaBH₄, CH₃OH)

XIV → XV (p-TSA, Molecular Sieves, Toluene)

XV → XVI (H₂, 5% Pd/C, C₂H₅OH)

XVI → XVII (CO₂, n-BuLi, −78° C., THF)

XVII → XVIII ((C₆H₅O)₂P(O)N₃, (C₂H₅)₃N, t-BuOH)

Schema 5 -continued

XVIII → XIX (CF₃COOH)

XIX → XX (NCS/DMF) where X is Cl

Schema 6 where Y is F, with HOC(CH₃)₂C≡CH, KOH, DMSO

→ XXI

XXI → XXII (180° C., with o-dichlorobenzene)

XXII → XXIII (KOH, t-BuOH)

XXIII → XXIV (NaOCl, NaOH, H₂O, Dioxane)

XXIV → XXVI (5% Pd/C, C₂H₅OH)

XXVI → (NCS, DMF)

XXIV → (NCS, DMF)

Schema 6

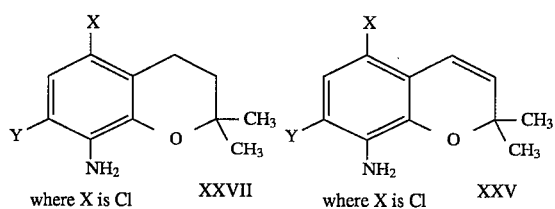

Schema 7

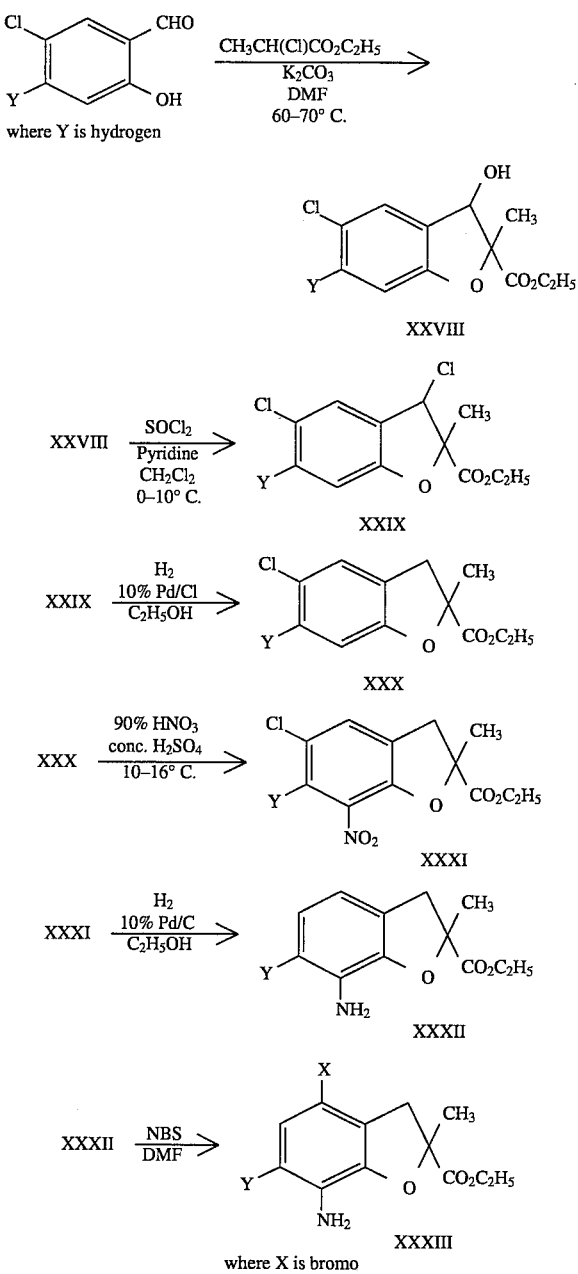

Schema 8

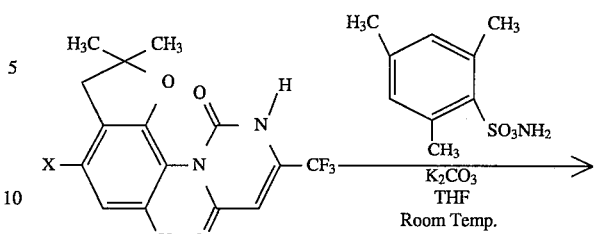

In Schema 1, a 3,5-optionally substituted-2-nitrophenol is reacted with a 2-alkenyl chloride, such as 2-methallyl chloride, to form the corresponding 2-(2-alken-1-yloxy)-4,6-optionally substituted-nitrobenzene (I), for example, 4-chloro-2-(2-methyl-2-propen-1-yloxy)nitrobenzene. This product is rear-ranged by heating to 180° C. to give the corresponding 2-(2-alken-1-yl)-6-nitrophenol (II), for example, 3-chloro-2-(2-methyl-2-propen-1-yl)-6-nitrophenol. This compound is then heated in the presence of p-toluenesulfonic acid to give the corresponding 7-nitrobenzofuran (III), for example 4-chloro-2,3-dihydro-2,2-dimethyl-7-nitrobenzofuran. Compound III is then converted to the corresponding amine(IV) by reduction of the nitro group using powdered iron, acetic acid, and water, after which the amine is heated at reflux with trichloromethyl chloroformate to form the corresponding isocyanate(V). The isocyanate is then treated with a 3-amino-3-fluoroalkylacrylate, for example, ethyl 3-amino-4,4,4-trifluorocrotonate, to give the corresponding 3-(2,3-dihydrobenzofuran-7-yl)-6-haloalkyl uracil, for example, 3-(4-chloro-2,3-dihydro-2,2-dimethylbenzofuran-7-yl)-6-trifluoromethyluracil. This uracil which represents certain compounds of this invention may be isolated, or without isolation, may be alkylated with an alkyl iodide, such as methyl iodide, in the presence of anhydrous potassium carbonate to produce the corresponding 3-(2,3-dihydrobenzofuran-7-yl)-1-alkyl-6-haloalkyluracil (VI), for example 3-(4-chloro-2,3-dihydro-2,2-dimethylbenzofuran-7-yl)-1-methyl-6-trifluoromethyluracil.

Schema 2 illustrates the formation of a 3-(2,3-dihydro-4,6-optionally substituted-benzofuran-3-on-7-yl)-6-haloalkyluracil, such as 3-(2,3-dihydro-2,2-dimethyl-4-methoxybenzofuran-3-on-7-yl)-1-methyl-6-trifluoromethyl uracil by oxidizing the corresponding 3-(2,3-dihydrobenzofuran-7-yl)-6-halo-alkyluracil with potassium persulfate and copper (II)sulfate pentahydrate in acetonitrile and water.

Schema 3 illustrates an alternative method of producing the above benzofuranyl-3-on-7-yl uracils by the oxidation of a 2,3-dihydro-4,6-optionally disubstituted-7-nitrobenzofuran (Compound III in Schema 1). The 2,3-dihydro-7-nitrobenzofuran is treated with N-bromosuccinimide while being irradiated with light. The product of this reaction, a 3-bromo-7-nitrobenzofuran (VIII), is then reacted with silver tetrafluoroborate in dimethyl sulfoxide in the presence of triethylamine, yielding the corresponding 2,3-dihydro-7-nitrobenzofuran-3-one (IX). This compound may be used in place of compound III in Schema I to produce the corresponding 3-(2,3-dihydrobenzofuran-3-on-7-yl)-1-alkyl-6-haloalkyluracil.

Schema 4 illustrates an alternative process for preparing the uracils of this invention in which a 7-amino-2,3-dihydrobenzofuran, for example, 7-amino-4-chloro-2,3-dihydro-2,2-dimethylbenzofuran, is successively treated with trichloromethyl chloroformate and then ethanol to give the corresponding ethyl N-(2,3-dihydrobenzofuran-7-yl)carbamate (X). The carbamate is then reacted with sodium hydride and a 3-amino-3-fluoroalkylacrylate, for example, ethyl 3-amino-4,4,4-trifluorocrotonate, and subsequently with an alkyl iodide and potassium carbonate to produce the 3-(2,3-dihydrobenzofuran-7-yl)-1-alkyl-6-haloalkyluracil, for example, 3-(4-chloro-2,3-dihydro-2,2-dimethylbenzofuran-7-yl)-1-methyl-6-trifluoromethyluracil (VI). The 3-(2,3-dihydrobenzofuran-3-on-7-yl)-1-alkyl-6-haloalkyluracils of this invention may be prepared using an analogous method.

Schema 5 illustrates the synthesis of an amino substituted 3,4-dihydro-2H-1-benzopyran, for example, 8-amino-5-chloro-3,4-dihydro-7-fluoro-2H-1-benzopyran, starting with the reaction of an appropriately halo-substituted phenol with 3-bromopropanol under basic conditions in acetone, yielding the corresponding substituted phenoxypropanol (XI). The propanol is oxidized with Jones reagent in water and acetone, giving an acid, for example, 3-(3-fluorophenoxy)propanecarboxylic acid (XII). The acid is in turn cyclized with phosphorous pentachloride and aluminium chloride in methylene chloride, affording the corresponding 3,4-dihydro-7-substituted-2H-1-benzopyran-4-one (XIII), which is then treated with sodium borohydride in methanol, yielding the appropriate 3,4-dihydro-7-substituted-4-hydroxy-2H-1-benzopyran, for example, 3,4-dihydro-7-fluoro-4-hydroxy-2H-1-benzopyran (XIV). The 4-hydroxybenzopyran is dehydrated with molecular sieves in the present of p-toluenesulfonic acid, yielding the corresponding 7-fluoro-2H-1-benzopyran (XV). This compound is then hydrogenated in the presence of 5% palladium on carbon in ethanol, yielding 3,4-dihydro-7-fluoro-2H-1-benzopyran (XVI), which is in turn treated with n-butyllithium and carbon dioxide at −78° C. in tetrahydrofuran, affording the corresponding 3,4-dihydro-7-fluoro-2H-1-benzopyran-8-ylcarboxylic acid (XVII). The so-prepared acid is then refluxed with diphenylphosphoryl azide under mild basic conditions in t-butanol, giving the corresponding 1,1-dimethylethyl N-(3,4-dihydro-7-fluoro-2H-1-benzopyran-8-yl)carbamate (XVIII). The carbamate is then converted to the free amine by treating it with trifluoroacetic acid, yielding the 8-amino-3,4-dihydro-7-fluoro-2H-1-benzopyran intermediate (XIX). The intermediate benzopyran is optionally halogenated in the 5-position by treatment with, for example, N-chlorosuccinimide in N,N-dimethylformamide, yielding the desired 8-amino-5-chloro-3,4-dihydro-7-fluoro-2H-1-benzopyran (XX) intermediate. Examples 11 and 12 provide detailed descriptions of how these compounds are prepared.

Schema 6 illustrates the synthesis of an amino substituted 2,2-dialkyl-2H-1-benzopyran and an amino substituted 2,2-dialkyl-3,4-dihydro-2H-1-benzopyran, for example, 8-amino-5-chloro-7-fluoro-2H-1-benzopyran and 8-amino-5-chloro-3,4-dihydro-7-fluoro-2H-1-benzopyran by the reaction of an appropriately substituted 2-fluorobenzonitrile with 2-methyl-3-butyn-2-ol under basic conditions in dimethyl sulfoxide, yielding the corresponding 3-(2-cyano-substituted-phenoxy)-3-methyl-1-butyne (XXI). The butyne intermediate is then cyclized at 180° C. in 1,2-dichlorobenzene, giving the appropriate 8-cyano-2,2-dialkyl-7-fluoro-2H-1-benzopyran, for example, 8-cyano-2,2-dimethyl-7-fluoro-2H-1-benzopyran (XXII), which is in turn treated with potassium hydroxide in t-butanol, yielding 2,2-dimethyl-7-fluoro-2H-1-benzopyran-8-ylcarboxamide (XXIII). The so-prepared carboxamide is then reduced with sodium hypochlorite and sodium hydroxide in water and dioxane, affording the corresponding free amine, for example, 8-amino-2,2-dimethyl-7-fluoro-2H-1-benzopyran (XXIV). The intermediate benzopyran is optionally halogenated in the 5-position as described above, yielding the corresponding benzopyran intermediate, for example, 8-amino-5-chloro-2,2-dimethyl-7-fluoro-2H-1-benzopyran (XXV). To obtain an amino substituted 2,2-dialkyl-3,4-dihydro-2H-1-benzopyran, for example, 8-amino-5-chloro-3,4-dihydro-7-fluoro-2H-1-benzopyran, the benzopyran (XXIV), described above, is first hydrogenated in the presence of 5% palladium on carbon in ethanol. The so-prepared 8-amino-3,4-dihydro-7-fluoro-2H-1-benzopyran (XXVI) is then optionally halogenated in the 5-position, affording the desired 8-amino-5-chloro-3,4-dihydro-7-fluoro-2H-1-benzopyran (XXVII). Examples 13 and 14 provide detailed descriptions of how these compounds are prepared.

Schema 7 illustrates the synthesis of an amino substituted 2,3-dihydro-2-alkoxycarbonyl-2-alkylbenzofuran, for example, 7-amino-2-ethoxycarbonyl-2,3-dihydro-2-methylbenzofuran by the cyclization of 5-chloro-2-hydroxybenzaldehyde with an alkyl 2-chloropropionate, for example, ethyl 2-chloropropionate, under basic conditions in N,N-dimethylformamide at 60°–70° C., affording the corresponding 5-chloro-2-ethoxycarbonyl-2,3-dihydro-3-hydroxy-2-methylbenzofuran (XXVII). The so-prepared benzofuran is chlorinated with thionyl chloride in the presence of pyridine in methylene chloride at 0°–10° C., then dechlorinated by treatment with hydrogen in the presence of 10% palladium on carbon in ethanol, yielding the corresponding 3-unsubstituted intermediate 5-chloro-2-ethoxycarbonyl-2,3-dihydro-2-methylbenzofuran (XXX). The 3-unsubstituted benzofuran is in turn nitrated with 90% nitric acid and concentrated sulfuric acid at 10°–16° C., affording 5-chloro-2-ethoxycarbonyl-2,3-dihydro-2-methyl-7-nitrobenzofuran (XXXI), which is then hydrogenated in the presence of 10% palladium on carbon in ethanol, affording the free amine intermediate 7-amino-2-ethoxycarbonyl-2,3-dihydro-2-methylbenzofuran ((XXXII). The so-prepared intermediate is optionally halogenated with, for example, N-bromosuccinimide in N,N-dimethylformamide, affording the corresponding 7-amino-4-bromo-2-ethoxycarbonyl-2,3-dihydro-2-methylbenzofuran (XXXIII) intermediate.

Schema 8 illustrates the formation of a 1-amino-3-(benzoheterocyclyl)uracil, such as 1-amino-3-(4-chloro-2,3-dihydro-2,2-dimethylbenzofuran-7-yl)-6-trifluoromethyluracil for the treatment of the corresponding 3-(4-chloro-2,3-dihydro-2,2-dimethylbenzofuran-7-yl)-6-trifluoromethyluracil with 1-aminooxysulfonyl-2,4,6-trimethylbenzene and potassium bicarbonate in tetrahydrofuran at ambient temperature.

Methods of preparing the compounds of this invention are further illustrated in the following nonlimiting Examples.

EXAMPLE 1

SYNTHESIS OF
3-(4-CHLORO-2,3-DIHYDRO-2,2-DIMETHYLBENZOFURAN-7-YL
)-1-METHYL-6-TRIFLUOROMETHYLURACIL
(Compound 3)

Step A

Synthesis of 5-chloro-2-nitrophenol

A 1M solution of boron tribromide in methylene chloride (400 mL, 0.40 mole) was cooled to −20° C. A solution of 37.5 g (0.20 mole) of 5-chloro-2-nitroanisole in 200 mL of methylene chloride was added slowly to the first solution. Upon completion of addition, the mixture was allowed to warm to ambient temperature at which it stirred for about 16 hours. At the conclusion of this period the reaction mixture was poured into ice water. The organic layer was separated from the aqueous layer and was evaporated under reduced pressure, leaving 31.40 g of 5-chloro-2-nitrophenol as a solid residue, m.p. 38°–39° C.

Step B

Synthesis of
4-chloro-2-(2-methyl-2-propen-1-yloxy)nitrobenzene

A mixture of 30.0 g (0.17 mole) of 5-chloro-2-nitrophenol, 30.49 g (0.221 mole) of potassium carbonate, and 18.47 g (0.204 mole) of 2-methyl-2-propen-1-ol in 200 mL of 2-butanone was heated at 80° C. for approximately 16 hours. During this period the reaction changed color from orange to pale yellow. At the conclusion of this period the reaction mixture was filtered, and the filtrate was evaporated under reduced pressure, leaving 32.50 g of 4-chloro-2-(2-methyl-2-propen-1-yloxy)nitrobenzene as a solid residue, m.p. 47°–49° C.

Step C

Synthesis of
3-chloro-2-(2-methyl-2-propen-1-yl)-6-nitrophenol

In a flask 30.0 g (0.14 mole) of 4-chloro-2-(2-methyl-2-propen-1-yloxy)nitrobenzene was heated at 180° C. for approximately 16 hours. At the conclusion of this period the reaction mixture was cooled to ambient temperature and was passed through a column of silica gel, eluting with methylene chloride. Product-containing fractions were combined and evaporated under reduced pressure, yielding 20.0 g of 3-chloro-2-(2-methyl-2-propen-1-yl)-6-nitrophenol as an oil. A second set of product-containing fractions was combined and evaporated under reduced pressure, yielding 8.9 g of 4-chloro-2,3-dihydro-2,2-dimethyl-7-nitrobenzofuran.

Step D

Synthesis of
4-chloro-2,3-dihydro-2,2-dimethyl-7-nitrobenzofuran

A mixture of 20.0 g (0.088 mole) of 3-chloro-2-(2-methyl-2-propen-1-yl)-6-nitrophenol and 0.35 g (0.002 mole) of p-toluenesulfonic acid in 100 mL of xylene was heated at reflux for approximately 16 hours. The solvent was evaporated under reduced pressure, leaving a residue which was passed through a column of silica gel, eluting with methylene chloride. The product-containing fractions were combined, washed with an aqueous solution of sodium hydroxide, dried over anhydrous magnesium sulfate, and the solvent evaporated under reduced pressure, yielding 16.85 g of 4-chloro-2,3-dihydro-2,2-dimethyl-7-nitrobenzofuran as an oil.

Step E

Synthesis of
7-amino-4-chloro-2,3-dihydro-2,2-dimethylbenzofuran

A solution of 4.0 g (0.018 mole) of 4-chloro-2,3-dihydro-2,2-dimethyl-7-nitrobenzofuran in approximately 60 mL of glacial acetic acid was heated to 50° C. To this solution were added 10 mL of water, and, while maintaining the temperature at 50° C., 4.0 g (0.072 mole) of powdered iron. Upon completion of addition, the reaction mixture was allowed to cool to room temperature at which it stirred for an hour. Then the reaction mixture was diluted with 100 mL of water and filtered. The filtrate was extracted with diethyl ether, and the combined extracts were dried over anhydrous magnesium sulfate and filtered. The solvent was evaporated from this filtrate under reduced pressure, leaving 2.45 g of 7-amino-4-chloro-2,3-dihydro-2,2-dimethylbenzofuran as a residue.

Step F

Synthesis of
4-chloro-2,3-dihydro-2,2-dimethylbenzofuran-7-yl isocyanate

To a solution of 1.97 g (0.010 mole) of 7-amino-4-chloro-2,3-dihydro-2,2-dimethylbenzofuran in 60 mL of toluene was added slowly 1.2 mL (0.010 mole) of trichloromethyl chloroformate. This mixture was stirred at ambient temperature for one hour and then was heated at reflux for approximately 16 hours. At the conclusion of this period the solvent was evaporated from the reaction mixture under reduced pressure, leaving 2.23 g of 4-chloro-2,3-dihydro-2,2-dimethylbenzofuran-7-yl isocyanate as an oil.

Step G

Synthesis of
3-(4-chloro-2,3-dihydro-2,2-dimethylbenzofuran-7-yl)-1-methyl-6-trifluoromethyluracil A mixture of 0.40 g (0.01 0 mole) of sodium hydride and 1.83 g (0.10 mole) of ethyl 3-amino-4,4,4-trifluorocrotonate was cooled to –20° C. To this mixture was slowly added 2.23 g (0.01 mole) of 4-chloro-2,3-dihydro-2,2-dimethylbenzofuran- 7-yl isocyanate. Upon completion of addition, the reaction mixture was allowed to warm to ambient temperature at which it was stirred for one hour. At the conclusion of this period the reaction mixture was heated to 85° C. at which it was stirred for approximately 16 hours. Then 1.38 g (0.01 mole) of potassium carbonate and 2.80 g (0.020 mole) of methyl iodide were added to the reaction mixture, and it was heated at 75° C. for seven hours. At the conclusion of this period the mixture was filtered, and the filtrate diluted with 200 mL of water. This mixture was extracted with diethyl ether. The extracts were dried over anhydrous magnesium sulfate, filtered, and the solvent evaporated from the filtrate under reduced pressure, leaving a yellow oil as residue. This oil was passed through a column of silica gel, eluting with methylene chloride:heptane (70:30). Product-containing fractions were combined, and the solvent was evaporated under reduced pressure, leaving a solid residue. This residue was washed with petroleum ether, yielding 1.50 g of 3-(4-chloro-2,3-dihydro-2,2-dimethylbenzofuran-7-yl)-1-methyl-6-trifluoromethyluracil (Compound 3), m.p. 152°–153° C. The NMR spectrum was consistent with the proposed structure.

EXAMPLE 2

SYNTHESIS OF
3-(4-CHLORO-2,3-DIHYDRO-2,2-DIMETHYLBENZOFURAN-3-ON-7-YL)-1-METHYL-6-TRIFLUOROMETHYLURACIL (Compound 8)

Step A

Synthesis of
3-bromo-4-chloro-2,3-dihydro-2,2-dimethyl-7-nitrobenzofuran

A mixture of 11.82 g (0.052 mole) of 4-chloro-2,3-dihydro-2,2-dimethyl-7-nitrobenzofuran (Example 1, Step C) and 9.3 g (0.052 mole) of N-bromosuccinimide in 200 mL of carbon tetrachloride was irradiated with a sun lamp for approximately 16 hours. No reaction occurred during this time. To this mixture was then added 0.10 g of benzoyl peroxide, and the reaction mixture was then heated at reflux and irradiated simultaneously for a period of five hours. The sun lamp was turned off, and the mixture was allowed to stir while being heated at reflux for an additional hour. The mixture was then passed through a column of silica gel, and product-containing fractions were combined. The solvent was evaporated from the combined fractions under reduced pressure, leaving 15.2 g of 3-bromo-4-chloro-2,3-dihydro-2,2-dimethyl-7-nitrobenzofuran as a solid, m.p. 103°–104° C.

Step B

Synthesis of 4-chloro-2,3-dihydro-2,2-dimethyl-7-nitrobenzofuran-3-one

A solution of 15.0 g (0.0489 mole) of 3-bromo-4-chloro-2,3-dihydro-2,2-dimethyl-7-nitrobenzofuran in 100 mL of dimethyl sulfoxide was added slowly to a mixture of 9.73 g (0.050 mole) of silver tetrafluoroborate in 100 mL of dimethyl sulfoxide. Upon completion of addition, 5.0 g (0.050 mole) of triethylamine was added to the reaction mixture, and stirring was continued for approximately 16 hours at ambient temperature. At the conclusion of this period the reaction mixture was heated at 60° C. for one hour and then cooled to ambient temperature. The mixture was filtered, and the filtrate was poured into 200 mL of water. This mixture was extracted with diethyl ether. The extract was dried over anhydrous magnesium sulfate, filtered, and the solvent was evaporated from the filtrate under reduced pressure, leaving a residue. This residue was passed through a column of silica gel, yielding 5.35 g of 4-chloro-2,3-dihydro-2,2-dimethyl-7-nitrobenzofuran-3-one as a solid residue, m.p. 167°–168° C.

Step C

Synthesis of 7-amino-4-chloro-2,3-dihydro-2,2-dimethylbenzofuran-3-one

By the method of Example 1, Step E, 4.82 g (0.020 mole) of 4-chloro-2,3-dihydro-2,2-dimethyl-7-nitrobenzofuran-3-one and 5.0 g of powdered iron were reacted in 80 mL of glacial acetic acid and 10 mL of water, yielding 3.25 g of 7-amino-4-chloro-2,3-dihydro-2,2-dimethylbenzofuran-3-one as an oil which subsequently solidified, m.p. 71°–73° C.

Step D

Synthesis of 4-chloro-2,3-dihydro-2,2-dimethylbenzofuran-3-on-7-yl isocyanate

By the method of Example 1, Step F, 2.70 g (0.012 mole) of 7-amino-4-chloro-2,3-dihydro-2,2-dimethylbenzofuran-3-one was reacted with 2.37 g (0.012 mole) of trichloromethyl chloroformate in toluene, yielding 2.85 g of 4-chloro-2,3-dihydro-2,2-dimethylbenzofuran-3-on-7-yl isocyanate.

Step E

Synthesis of 3-(4-chloro-2,3-dihydro-2,2-dimethylbenzofuran-3-on-7-yl)-1-methyl-6-trifluoromethyluracil By the method of Example 1, Step G, 2.85 g (0.0112 mole) of 4-chloro-2,3-dihydro-2,2-dimethylbenzofuran-3-on-7-yl isocyanate was reacted with 46 g (0.012 mole) of sodium hydride and 2.20 g (0.012 mole) ethyl 3-amino-4,4,4-trifluorocrotonate in tetrahydrofuran. Subsequently, 3.0 g (0.021 mole) of methyl iodide and 1.65 g (0.012 mole) of potassium carbonate were reacted with the product of the first reaction, yielding 1.75 g of 3-(4-chloro-2,3-dihydro-2,2-dimethylbenzofuran-3-on-7-yl)-1-methyl-6-trifluoromethyluracil (Compound 8) as a solid, m.p. 177°–178° C. The NMR spectrum was consistent with the proposed structure.

| Elemental analysis: | Carbon | Hydrogen | Nitrogen |
|---|---|---|---|
| Calculated: | 49.43 | 3.11 | 7.20 |
| Found: | 48.98 | 2.81 | 6.88 |

Example 3

SYNTHESIS OF 3-(4,6-DICHLORO-2,3-DIHYDRO-2,2-DIMETHYLBENZOFURAN-3-ON-7-YL)-1-METHYL-6-TRIFLUOROMETHYLURACIL (Compound 22)

Step A

Synthesis of 2,3-dihydro-2,2-dimethyl-7-nitrobenzofuran-3-one

A mixture of 37.3 g (0.193 mole) of 2,3-dihydro-2,2-dimethyl-7-nitrobenzofuran, 156.6 g (0.58 mole) of potassium persulfate, and 48.2 g (0.193 mole) of copper(II) sulfate pentahydrate in 500 mL of acetonitrile and 500 mL of water was prepared. This mixture was heated at reflux for one hour with vigorous stirring. The reaction mixture was cooled and then extracted three times with methylene chloride. The combined extracts were dried over anhydrous magnesium sulfate, filtered, and the solvent was evaporated from the filtrate under reduced pressure, leaving 37.4 g of 2,3-dihydro-2,2-dimethyl-7-nitrobenzofuran-3-one as a residue. The NMR and IR spectra of the same product from a previous run of this reaction were consistent with the proposed structure.

Step B

Synthesis of 7-amino-2,3-dihydro-2,2-dimethylbenzofuran-3-one

By the method of Example 1, Step E, 20.0 g (0.097 mole) of 2,3-dihydro-2,2-dimethyl-7-nitrobenzofuran-3-one and 27.0 g (0.483 mole) of powdered iron were reacted in 85 mL of glacial acetic acid and 15 mL of water, yielding 11.79 g of 7-amino-2,3-dihydro-2,2-dimethylbenzofuran-3-one, m.p. 80°–84° C. The NMR and IR spectra of this product were consistent with the proposed structure.

Step C

Synthesis of 7-amino-4,6-dichloro-2,3-dihydro-2,2-dimethylbenzofuran-3-one

A solution of 6.10 g (0.0344 mole) of 7-amino-2,3-dihydro-2,2-dimethylbenzofuran-3-one in 80 mL of N,N-dimethylformamide was cooled to 0° C., and 6.90 g (0.052 mole) of N-chlorosuccinimide was added in several small portions. This mixture was stirred for approximately 16 hours at ambient temperature. At the conclusion of this period the reaction mixture was poured into water, and this mixture was extracted three times with diethyl ether. The combined extracts were washed with a 10% aqueous solution of lithium chloride, dried over anhydrous magnesium sulfate, and concentrated under reduced pressure, leaving a yellow, semisolid residue. This solid was passed through a column of silica gel, eluting with ethyl acetate:heptane (30:70). Three different materials were separated, and the 5 fractions containing each were combined. The solvent was evaporated from each of these combined fractions. The NMR spectra were consistent with these products being (in order of elution): 7-amino-6-chloro-2,3-dihydro-2,2-dimethylbenzofuran-3-one, 7-amino-4,6-dichloro-2,3-dihydro-2,2-dimethyl-benzofuran- 3-one, and 7-amino-4-chloro-2,3-dihydro-2,2-dimethylbenzofuran-3-one. The second material was contaminated with the first. The two fractions were combined and passed simultaneously through a column of silica gel, eluting with methylene chloride. Product-containing fractions were combined, and the solvent was evaporated under reduced pressure. This procedure yielded 4.55 g of 7-amino-4,6-dichloro-2,3-dihydro-2,2-dimethylbenzofuran- 3-one as a pale yellow solid, m.p. 168.5°–170° C. A second set of fractions was combined and concentrated under reduce pressure, yielding 1.60 g of 7-amino-6-chloro-2,3-dihydro-2,2-dimethylbenzofuran-3-one as a yellow solid, m.p. 91.5°–93.5° C. The third product from the first chromatographic separation was purified by passing it separately through a column of silica gel, eluting with methylene chloride. This produced 0.92 g of 7-amino-4-chloro-2,3-dihydro-2,2-dimethylbenzofuran-3-one as a viscous, pale yellow oil which subsequently solidified, m.p. 80°–82° C. The NMR spectra of all three products were consistent with the proposed structures.
Step D Synthesis of
4,6-dichloro-2,3-dihydro-2,2-dimethylbenzofuran-3-on-7-yl isocyanate To a solution of 4.00 g (0.0163 mole) of 7-amino-4,6-dichloro-2,3-dihydro-2,2-dimethylbenzofuran-3-one in 80 mL of toluene at ambient temperature was added 3.22 g (0.0163 mole) of trichloromethyl chloroformate. This mixture was stirred for fifteen minutes before being heated at reflux for three hours. The solvent was evaporated under reduced pressure, leaving 4,6-dichloro-2,3-dihydro-2,2-dimethylbenzofuran-3-on-7-yl isocyanate as a pale yellow oil. Upon standing, this oil solidified. The IR spectrum was consistent with an isocyanate. Step E Synthesis of 3-(4,6-dichloro-2,3-dihydro-2,2-dimethylbenzofuran-3-on-7-yl)-6-trifluoromethyluracil A 60% dispersion of sodium hydride in mineral oil (0.78 g, 0.019 mole) was placed in a flask, and the mineral oil was removed from it with two heptane washes. The sodium hydride was suspended in 40 mL of dry tetrahydrofuran, and this suspension was cooled to 0°–10° C. A solution of 2.96 g (0.0162 mole) of ethyl 3-amino-4,4,4-trifluorocrotonate in 5 mL of dry tetrahydrofuran was added dropwise to the suspension of sodium hydride. This mixture was then stirred at ambient temperature for 30 minutes. A solution of 4.40 g (0.0162 mole) of 4,6-dichloro-2,3-dihydro-2,2-dimethylbenzofuran- 3-on-7-yl isocyanate in 10 mL of dry tetrahydrofuran was added dropwise. Upon completion of addition, the reaction mixture was stirred at ambient temperature for 30 minutes and then was heated at reflux for three hours. At the conclusion of this period the mixture was diluted with water, and the resulting mixture was extracted three times with ethyl acetate. The combined extracts were dried over anhydrous magnesium sulfate, filtered, and the filtrate was evaporated under reduced pressure, yielding 9.58 g of a gummy, pale yellow residue. This residue was triturated with methylene chloride, yielding 4.79 g of 3-(4,6-dichloro-2,3-dihydro-2,2-dimethylbenzofuran-3-on-7-yl)-6-trifluoromethyluracil as an off-white solid, m.p. 308°–320° C. The NMR and IR spectra were consistent with the proposed structure.
Step F Synthesis of
3-(4,6-dichloro-2,3-dihydro-2,2-dimethylbenzofuran-3-on-7-yl)-1-methyl-6-trifluoromethyluracil A solution of 1.50 g (0.0037 mole) of 3-(4,6-dichloro-2,3-dihydro-2,2-dimethylbenzofuran-3-on-7-yl)-6-trifluoromethyluracil in 80 mL of dry tetrahydrofuran was prepared, and to it were added 0.58 g (0.0041 mole) of methyl iodide, 0.61 g (0.0044 mole) of potassium carbonate, and 0.20 g of 1,4,7, 10, 13, 16-hexaoxacyclooctadecane. This mixture was heated at reflux for approximately 16 hours. After being cooled, water was added to the reaction mixture which was then extracted three times with 70 mL of ethyl acetate. The extracts were combined, dried over anhydrous magnesium sulfate, and filtered. The filtrate was concentrated under reduced pressure, yielding 1.53 g of a pale yellow, solid residue. This solid was passed through a column of silica gel, eluting with ethyl acetate:heptane (30:70). The product-containing fractions were combined and evaporated under reduced pressure, yielding 1.20 g of 3-(4,6-dichloro-2,3-dihydro-2,2-dimethylbenzofuran-3-on-7-yl)-1-methyl-6-trifluoromethyluracil (Compound 22) as a white solid, m.p. 186°–187° C. The NMR and IR spectra were consistent with the proposed structure.

EXAMPLE 4

SYNTHESIS OF
3-(2,3-DIHYDRO-2,2-DIMETHYL-4-METHOXYBENZOFURAN-3-ON-7-YL)-1-METHYL-6-TRIFLUOROMETHYLURACIL (Compound 24)

Step A

Synthesis of 2,3-dihydro-2,2-dimethyl-4-methoxy-7-nitrobenzofuran

A solution of 11.3 g (0.054 mole) of 2,3-dihydro-2,2-dimethyl-4-fluoro-7-nitrobenzofuran (prepared by the method of Example 1, Steps B, C, and D, starting from 5-fluoro-2-nitrophenol) in 80 mL of dimethyl sulfoxide was prepared. To it was added 5.63 g (0.080 mole) of potassium methoxide. The resulting mixture was stirred for approximately 16 hours at ambient temperature under a nitrogen atmosphere. At the conclusion of this period the reaction mixture was diluted with water and then extracted three times with ethyl acetate. The extracts were combined, washed with a saturated aqueous solution of sodium chloride, dried over anhydrous magnesium sulfate, and filtered. Evaporation of the filtrate under reduced pressure yielded 10.20 g of a brown oil which solidified on standing. This solid was passed through a column of silica gel, eluting with ethyl acetate:heptane (20:80). The product-containing fractions were combined, and the solvent was evaporated under reduced pressure, yielding 2.80 g of 2,3-dihydro-2,2-dimethyl-4-methoxy-7-nitrobenzofuran as pale yellow, needle-shaped crystals, m.p. 135°–136° C. The NMR and IR spectra were consistent the proposed structure. This reaction was repeated to obtain more product for succeeding reactions.

Step B

Synthesis of 7-amino-2,3-dihydro-2,2-dimethyl-4-methoxybenzofuran

In a Parr hydrogenation bottle were placed 4.50 g (0.020 mole) of 2,3-dihydro-2,2-dimethyl-4-methoxy-7-nitrobenzofuran, 0.30 g of platinum oxide, and 250 mL of ethanol. Hydrogen gas was introduced into this bottle until absorption of it ceased. The mixture was then filtered to remove the platinum oxide catalyst, and the filtrate was evaporated under reduced pressure, leaving a residue. The NMR and IR spectra of this residue were consistent with the proposed structure. This residue was passed through a column of silica gel. Product-containing fractions were combined into two fractions. The first of these was concentrated under reduced pressure to yield 2.22 g of a dark violet, viscous oil. The second fraction was similarly concentrated, yielding 1.65 g of a violet, viscous oil. The total yield of 7-amino-2,3-dihydro-2,2-dimethyl-4-methoxybenzofuran was 3.87 g.

Step C

Synthesis of 2,3-dihydro-2,2-dimethyl-4-methoxybenzofuran-7-yl isocyanate

By the method of Example 1, Step F, 3.70 g (0.0191 mole) of 7-amino-2,3-dihydro-2,2-dimethyl-4-methoxybenzofuran and 3.79 g (0.0191 mole) of trichloromethyl chloroformate were reacted in 100 mL of toluene, yielding 2,3-dihydro-2,2-dimethyl-4-methoxybenzofuran-7-yl isocyanate as a brownish-yellow, viscous oil. The IR spectrum was consistent with the proposed structure.

Step D

Synthesis of 3-(2,3-dihydro-2,2-dimethyl-4-methoxybenzofuran-7-yl)-1-methyl-6-trifluoromethyluracil (Compound 5)

By the method of Example 1, Step G, 4.20 g (0.0192 mole) of 2,3-dihydro-2,2-dimethyl-4-methoxybenzofuran-7-yl isocyanate was reacted with 3.51 g (0.0192 mole) of ethyl 3-amino-4,4,4-trifluorocrotonate and 0.92 g (0.023 mole) of sodium hydride (60% in mineral oil) in 30 mL of dry tetrahydrofuran. The reaction mixture was concentrated, yielding a residue which was dissolved in 30 mL of N,N-dimethylformamide. To this solution were added 3.18 g (0.023 mole) of potassium carbonate and 2.72 g (0.0192 mole) of methyl iodide. This reaction yielded 1.60 g of 3-(2,3-dihydro-2,2-dimethyl-4-methoxybenzofuran-7-yl)-1-methyl-6-trifluoromethyluracil (Compound 5) as a brown solid, m.p. 201°–203° C. The NMR and IR spectra were consistent with the proposed structure.

Step E

Synthesis of 3-(2,3-dihydro-2,2-dimethyl-4-methoxybenzofuran-3-on-7-yl)-1-methyl-6-trifluoromethyluracil By the method of Example 3, Step A, 1.30 g (0.0037 mole) of 3-(2,3-dihydro-2,2-dimethyl-4-methoxybenzofuran-7-yl)-1-methyl-6-trifluoromethyluracil was reacted with 2.98 g (0.011 mole) of potassium persulfate and 0.92 g (0.0037 mole) of copper(11) sulfate pentahydrate in 40 mL of acetonitrile and 40 mL of water, yielding 0.90 g of 3-(2,3-dihydro-2,2-dimethyl-4-methoxybenzofuran-3-on-7-yl)-1-methyl-6-trifluoromethyluracil (Compound 24) as an off-white solid, m.p. 222.5°–224° C. The NMR and IR spectra were consistent with the proposed structure.

EXAMPLE 5

SYNTHESIS OF 3-(4,6-DICHLORO-2,3-DIHYDRO-2,2-DIMETHYL-3-METHOXYIMINOBENZOFURAN-7-YL)-1-METHYL-6-TRIFLUOROMETHYLURACIL (Compound 26)

In a flask were placed 3.20 g (0.0076 mole) of 3-(4,6-dichloro-2,3-dihydro-2,2-dimethylbenzofuran-3-on-7-yl)-1-methyl-6-trifluoromethyluracil, 1,20 g (0.0144 mole) of 0-methylhydroxylamine hydrochloride, 4 mL of ethanol, and 4 mL of pyridine. This mixture was heated at reflux for five hours and then was evaporated under reduced pressure, leaving a residue. The residue was dissolved in ethyl acetate, and this solution was washed with water. The aqueous washings were then extracted twice with ethyl acetate, and these extracts were combined with the ethyl acetate solution of the product. The combined extracts and solution was dried over anhydrous magnesium sulfate, filtered, and the solvent was evaporated from the filtrate under reduced pressure, leaving a light reddish, viscous oil as a residue. This oil was passed through a column of silica gel, eluting with methylene chloride. Product-containing fractions were combined, and the solvent evaporated under reduced pressure, leaving 0.73 g of 3-(4,6-dichloro-2,3-dihydro-2,2-dimethyl-3-methoxyiminobenzofuran-7-yl)-1-methyl-6-trifluoromethyluracil (Compound 26) as an off-white, fluffy solid, m.p. 145°–149° C. The NMR and IR spectra were consistent with the proposed structure.

EXAMPLE 6

SYNTHESIS OF 3-(4-CHLORO-2,3-DIHYDRO-2,2-DIMETHYL-6-FLUOROBENZOFURAN-3-ON-7-YL)-1-METHYL-6-TRIFLUOROMETHYLURACIL (Compound 21)

Step A

Synthesis of 6-fluoro-2-(2-methyl-2-propen-1-yloxy)benzonitrile

In a flask were placed 250.0 g (1.80 moles) of 2,6-difluorobenzonitrile, 129.8 g of (1.80 moles) of methallyl alcohol, and 1500 mL of dimethyl sulfoxide. This mixture was stirred vigorously while 124.76 g (1.89 moles) of 85% powdered potassium hydroxide was added in portions. This addition required 2 hours during which the temperature was maintained below 45° C. The reaction mixture was stirred at ambient temperature for approximately 21 hours. At the conclusion of this period the mixture was poured into 4 L of an ice/water mixture. This mixture was divided into two equal portions, and each was extracted twice with 1 L of ethyl acetate. The extracts were combined and washed twice with a saturated aqueous solution of sodium chloride. The extracts were dried over anhydrous magnesium sulfate and filtered. The filtrate was evaporated under reduced pressure leaving 302.7 g of 6-fluoro-2-(2-methyl-2-propen-1-yloxy)benzonitrile as a residue. The NMR spectrum was consistent with the proposed structure.

Step B

Synthesis of 7-cyano-2,3-dihydro-2,2-dimethyl-6-fluorobenzofuran

In a flask were placed 202.7 g (1.06 moles) of 6-fluoro-2-(2-methyl-2-propen-1-yloxy)benzonitrile and 4.0 g (0.042 mole) of anhydrous magnesium chloride. The temperature of the stirred reaction mixture was slowly for 30 minutes, the temperature was increased to 170° C. Thirty minutes later the temperature was raised to 185°–190° C. at which it was maintained for approximately 16 hours. At the conclusion of this period the reaction mixture was cooled to ambient temperature and was dissolved in methylene chloride. This solution was passed through a short column of silica gel, eluting with methylene chloride. Product-containing fractions were combined, and the solvent was evaporated under reduced pressure, yielding 174.08 g of 7-cyano-2,3-dihydro-2,2-dimethyl-6-fluorobenzofuran. The NMR spectrum was consistent with the proposed structure.

Step C

Synthesis of 2,3-dihydro-2,2-dimethyl-6-fluorobenzofuran-7-ylcarboxamide

In a flask were placed 140.0 g (0.732 mole) of 7-cyano-2,3-dihydro-2,2-dimethyl-6-fluorobenzofuran, 147.91 g (2.64 moles) of powdered potassium hydroxide, and 950 mL of t-butanol. This mixture was heated at reflux for 50 minutes after which it was cooled to ambient temperature. It was then poured into a mixture of 1500 mL of crushed ice and 1500 mL of a saturated aqueous solution of sodium chloride. The resulting mixture was extracted twice with 750 mL of ethyl acetate. The extracts were combined and washed once with a saturated aqueous solution of sodium chloride. After being dried over anhydrous magnesium sulfate and filtered, the solvent was evaporated from the filtrate under reduced pressure, yielding 136.09 g of 2,3-dihydro-2,2-dimethyl-6-fluorobenzofuran-7-ylcarboxamide. The NMR spectrum was consistent with the proposed structure.

Step D

Synthesis of 7-amino-2,3-dihydro-2,2-dimethyl-6-fluorobenzofuran

A solution of 56.1 g (1.4 moles) of sodium hydroxide in 3250 mL of water was prepared in a flask. To this solution was added 720 mL of 5.25% aqueous sodium hypochlorite. This solution was then cooled to 5° C. To the cooled solution was added a solution of 70.0 g (0.334 mole) of 2,3-dihydro-2,2-dimethyl-6-fluorobenzofuran-7-ylcarboxamide in 225 mL of dioxane. The addition was done in three portions during a five minute period, causing the temperature to increase to 15° C. The temperature was cooled to 5°–10° C. at which the reaction mixture was stirred for 30 minutes. At the conclusion of this period the reaction mixture was heated at 70°–75° C. for two hours. After being cooled to ambient temperature, the reaction mixture was extracted three times with diethyl ether, and the extracts were combined. The extract was washed three times with 500 mL of a saturated aqueous solution of sodium chloride, dried over anhydrous sodium sulfate, and filtered. The solvent was evaporated from the filtrate under reduced pressure, leaving a dark brown oil as a residue. This oil was passed through a column of silica gel, eluting with heptane:ethyl acetate (9:1). Product-containing fractions were combined, and the solvent evaporated under reduced pressure, yielding 40.58 g of 7-amino-2,3-dihydro-2,2-dimethyl-6-fluorobenzofuran. The NMR spectrum was consistent with the proposed structure.

Step E

Synthesis of 7-amino-4-chloro-2,3-dihydro-2,2-dimethyl-6-fluorobenzofuran

A solution of 39.27 g (0.217 mole) of 7-amino-2,3-dihydro-2,2-dimethyl-6-fluorobenzofuran in 750 mL of diethyl ether was cooled to −5° C to 0° C., and 23.54 g (0.217 mole) of t-butyl hypochlorite was added in a dropwise manner during a fifteen minute period. The temperature rose to 10° C., but was lowered to 0°–5° C. at which the reaction mixture stirred for 20 minutes. Gas chromatographic analysis showed that the reaction was incomplete, and an additional 4.54 g (0.042 mole) of t-butyl hypochlorite was added. The mixture was stirred at 0°–5° C. for an hour after which gas chromatographic analysis showed that the reaction was still incomplete. Therefore, an additional 1.82 g (0.017 mole) of t-butyl hypochlorite was added to the reaction mixture, and stirring was continued for one more hour. At the conclusion of this period the reaction was determined to have been completed, and it was poured into 400 mL of water. To this mixture was added 100 mL of 10% ammonium hydroxide. The aqueous and organic phases were separated. The aqueous phase was washed with diethyl ether, and this wash was combined with the organic phase. The combined material was dried over anhydrous sodium sulfate, filtered, and the solvent 20 evaporated from the filtrate under reduced pressure, leaving a dark red oil as the residue. This oil was passed through a column of silica gel, eluting with petroleum ether:diethyl ether (9:1). Product-containing fractions were combined, and the solvent was evaporated under reduced pressure, yielding 40.24 g of 7-amino-4-chloro-2,3-dihydro-2,2-dimethyl-6-fluorobenzofuran as a red oil. The NMR spectrum was consistent with the proposed structure.

Step F

Synthesis of ethyl N-(4-chloro-2,3-dihydro-2,2-dimethyl-6-fluorobenzofuran- 7-yl)carbamate To a stirred solution of 14.0 g (0.065 mole) of 7-amino-4-chloro-2,3-dihydro-2,2-dimethyl-6-fluorobenzofuran in toluene was added 13.8 g (0.070 mole) of trichloromethyl chloroformate. Upon completion of addition, the reaction mixture was stirred at ambient temperature for one hour and then was heated at reflux for approximately 21 hours. The solvent was evaporated from the reaction mixture under reduced pressure, and 40 mL of ethanol was added to the residue. This mixture was heated at 70°–80° C. for approximately 16 hours. The solvent was removed from this reaction mixture, leaving an oil as a residue. Mixing this oil with petroleum ether caused a tan solid, ethyl N-(4-chloro-2,3-dihydro-2,2-dimethyl-6-fluoro-benzofuran- 7-yl)carbamate, to form, m.p. 114°–115° C. The NMR was consistent with the proposed structure.

Step G

Synthesis of 3-(4-chloro-2,3-dihydro-2,2-dimethyl-6-fluorobenzofuran-7-yl)-1-methyl-6-trifluoromethyluracil The mineral oil was removed from 1.00 g (0.0251 mole) of 60% sodium hydride in mineral oil by washing twice with heptane under a nitrogen atmosphere and then adding 30 mL of N,N-dimethylformamide, creating a suspension which was cooled to 0° C. To this suspension was added dropwise a solution of 3.82 g (0.0209 mole) of ethyl 3-amino-4,4,4-trifluorocrotonate in 20 mL of N,N-dimethylformamide. Upon completion of addition, this mixture was stirred for 20 minutes at 0° C. A solution of 6.00 g (0.0209 mole) of ethyl N-(4-chloro-2,3-dihydro-2,2-dimethyl-6-fluorobenzofuran-7-yl)carbamate in 30 mL of N,N-dimethylformamide was added to the reaction mixture as it warmed to ambient temperature at which it was then stirred for 30 minutes. This reaction mixture was then heated at 100°–120° C. for approximately 16 hours after which it was cooled, diluted with 200 mL of a 10% aqueous solution of lithium chloride, and extracted twice with 100 mL of ethyl acetate. The combined extracts were washed with the 10% aqueous solution of lithium chloride, dried over anhydrous magnesium sulfate, and filtered. The filtrate was evaporated under reduced pressure, yielding 10.0 g of a viscous oil. To this viscous oil were added 80 mL of dry tetrahydrofuran, 4.38 g (0.0276 mole) of potassium carbonate, 4.12 g (0.0147 mole) of methyl iodide, and a small amount of 1,4,7, 10, 13,16-hexaoxacyclooctadecane. This reaction mixture was heated at reflux for three hours after which the solvent was evaporated under reduced pressure. The residue was diluted with water, and the resulting mixture was extracted three times with 100 mL of methylene chloride. The extracts were combined, dried over anhydrous magnesium sulfate, and filtered. The filtrate was evaporated under reduced pressure, yielding 9.00 g of a dark, viscous oil. This oil was passed through a column of silica gel, eluting with ethyl acetate-:heptane (30:70). Product-containing fractions were combined, and the solvent was evaporated under reduced pressure, yielding 5.54 g of 3-(4-chloro-2,3-dihydro-2,2-dimethyl-6-fluorobenzofuran-7-yl)-1-methyl-6-trifluoromethyluracil (Compound 5) as a tan solid. The NMR spectrum was consistent with the proposed structure.

Step H

Synthesis of 3-(4-chloro-2,3-dihydro-2,2-dimethyl-6-fluorobenzofuran-3-on-7-yl)-1-methyl-6-trifluoromethyluracil By the method of Example 3, Step A, 5.35 g (0.0137 mole) of 3-(4-chloro-2,3-dihydro-2,2-dimethyl-6-fluorobenzofuran-7-yl)-1-methyl-6-trifluoromethyluracil, 11.07 g (0.041 mole) of potassium persulfate, and 3.41 g (0.0137 mole) of copper(11) sulfate pentahydrate were reacted in 120 mL of acetonitrile and 120 mL of water, yielding 2.74 g of 3-(4-chloro-2,3-dihydro-2,2-dimethyl-6-fluorobenzofuran-3-on-7-yl)-1-methyl-6-trifluoromethyluracil (Compound 21) as an off-white solid, m.p. 160°–162° C. The NMR and IR spectra were consistent with the proposed structure.

EXAMPLE 7

SYNTHESIS OF 3-(4-CHLORO-2,3-DIHYDROBENZOFURAN-3-ON-7-YL)-1-METHYL-6-TRIFLUOROMETHYLURACIL (Compound 30)

Step A

Synthesis of methyl 3-nitrosalicylate

In a flask are placed 5.0 g (0.024 mole) of the sodium salt of 3-nitrosalicylic acid, 3.58g (0.0252 mole) of methyl iodide, and 40 mL of N,N-dimethylformamide. This mixture is stirred at ambient temperature for approximately sixteen hours. At the conclusion of this period 200 mL of a 10% aqueous solution of lithium chloride is added to the reaction mixture. This mixture is extracted three times with ethyl acetate. The combined extracts are washed with 200 mL of the 10% aqueous solution of lithium chloride, dried over anhydrous magnesium sulfate, and filtered. The filtrate is concentrated under reduced pressure, leaving a residue which is then passed through a column of silica gel, eluting with ethyl acetate. The product-containing fractions are combined, and the solvent is evaporated under reduced pressure leaving methyl 3-nitrosalicylate as a residue.

Step B

Synthesis of methyl 2-ethoxycarbonylmethoxy-3-nitrosalicylate

In a flask are placed 4.14 g (0.021 mole) of methyl 3-nitrosalicylate, 3.70 g (0.022 mole) of ethyl bromoacetate, 3.2 g (0.023 mole) of potassium carbonate, and 80 mL of N,N-dimethylformamide. The resulting mixture is heated at 90° C. for approximately 16 hours. At the conclusion of this period, the reaction mixture is cooled to room temperature, and 400 mL of a 10% aqueous solution of lithium chloride is added to the reaction mixture. The resulting mixture is extracted three times with ethyl acetate. The combined extracts are washed with 200 mL of the 10% aqueous solution of lithium chloride, dried over anhydrous magnesium sulfate, and filtered. The filtrate is concentrated under reduced pressure, leaving a residue which is then passed through a column of silica gel, eluting with ethyl acetate. The product-containing fractions are combined, and the solvent is evaporated under reduced pressure, leaving methyl 2-ethoxycarbonylmethoxy-3-nitrosalicylate as a residue.

Step C

Synthesis of ethyl 2,3-dihydro-7-nitrobenzofuran-3-on-2-ylcarboxylate

A 60% dispersion of sodium hydride in mineral oil (0.80 g, 0.020 mole) is placed in a flask, and the mineral oil is removed from it with two heptane washes. The sodium hydride is then suspended in 30 mL of N,N-dimethylformamide, and the suspension is cooled to 0°–10° C. To this suspension is added in a dropwise manner a solution of 4.53 g (0.016 mole) of methyl 2-ethoxycarbonylmethoxy-3-nitrosalicylate in 10 mL of N,N-dimethylformamide. Upon completion of addition, the reaction mixture is allowed to warm to ambient temperature at which it is stirred for approximately 16 hours. At the conclusion of this period, the reaction mixture is cooled and acidified with concentrated hydrochloric acid. Then 200 mL of a 10% aqueous solution of lithium chloride is added to the reaction mixture, and the resulting mixture is extracted three times with ethyl acetate. The combined extracts are washed with 100 mL of the 10% aqueous solution of lithium chloride, dried over anhydrous magnesium sulfate, and filtered. The filtrate is concentrated under reduced pressure, leaving a residue which is then passed through a column of silica gel, eluting with ethyl acetate. The product-containing fractions are combined, and the solvent is evaporated under reduced pressure, leaving ethyl 2,3-dihydro-7-nitrobenzofuran-3-on-2-ylcarboxylate as a residue.

Step D

Synthesis of 2,3-dihydro-7-nitro-3-benzofuranone

In a flask 3.77 g (0.015 mole) of ethyl 2,3-dihydro-7-nitrobenzofuran-3-on-2-ylcarboxylate is suspended in 75 mL of a 5% aqueous solution of sodium hydroxide which is heated at reflux until all solid has gone into solution. The solution is cooled to ambient temperature, and dilute sulfuric acid is added cautiously until there is no further evidence of decarboxylation. The product is extracted with ethyl acetate, and the combined extracts are dried over anhydrous magnesium sulfate and filtered. The filtrate is evaporated under reduced pressure, leaving 2,3-dihydro-7-nitro-3-benzofuranone as a residue.
Step E Synthesis of 7-amino-2,3-dihydro-3-benzofuranone By the method of Example 1, Step E, 2.51 g (0.014 mole) of 2,3-dihydro-7-nitro-3-benzofuranone is reacted with 3.1 g (0.056 mole) of powdered iron in 45 mL of glacial acetic acid and 8 mL of water, yielding 7-amino-2,3-dihydro-3-benzofuranone.
Step F Synthesis of 7-amino-4-chloro-2,3-dihydro-3-benzofuranone By the method of Example 3, Step C, 1.94 g (0.013 mole) of 7-amino-2,3-dihydro-3-benzofuranone and 1.74 g (0.013 mole) of N-chlorosuccinimide are reacted in 40 mL of N,N-dimethylformamide, yielding 7-amino-4-chloro-2,3-dihydro-3-benzofuranone.
Step G Synthesis of 4-chloro-2,3-dihydrobenzofuran-3-on-7-yl isocyanate By the method of Example 1, Step F, 2.2 g (0.012 mole) of 7-amino-4-chloro-2,3-dihydro-3-benzofuranone is reacted with 2.37 g (0.012 mole) of trichloromethyl chloroformate in 60 mL of toluene, yielding 4-chloro-2,3-dihydrobenzofuran-3-on-2-yl isocyanate.
Step H Synthesis of 3-(4-chloro-2,3-dihydrobenzofuran-3-on-7-yl)-1-methyl-6-trifluoromethyluracil (Compound 30)

By the method of Example 1, Step G, 2.10 g (0.010 mole) of 4-chloro-2,3-dihydrobenzofuran-3-on-7-yl isocyanate is reacted with 0.40 g (0.010 mole) of sodium hydride and 1.83 g (0.010 mole) of ethyl 3-amino-4,4,4-trifluorocrotonate, yielding 3-(4-chloro-2,3-dihydrobenzofuran-3-on-7-yl)-6-trifluoromethyluracil. This product is further reacted with 1.38 g (0.010 mole) of potassium carbonate and 2.80 g (0.020 mole) of methyl iodide, yielding 3-(4-chloro-2,3-dihydrobenzofuran-3-on-7-yl)-1-methyl-6-trifluoromethyluracil (Compound 30).

EXAMPLE 8

SYNTHESIS OF 3-SPIRO[CYCLOPROPANE-1,2'-4-CHLORO-2,3-DIHYDROBENZOFURAN-3-ON-7-YL]-1-METHYL-6-TRIFLUOROMETHYLURACIL (Compound 31)

Step A

Synthesis of spiro[cyclopropane-1,2'-2,3-dihydro-7-nitro-3-benzofuranone]

To a rapidly stirred solution of 3.66 g (0.0204 mole) of 2,3-dihydro-7-nitro-3-benzofuranone and 4.56 g (0.0406 mole) of potassium tert-butoxide in 40 mL of tert-butanol is added in small portions 4.8 g (0.019 mole) of 2-chloroethyl dimethyl sulfonium iodide (prepared by the method of W. von E Doering, K. Schreiber, *J. Am. Chem. Sec.* (1955), 77, 514). This mixture is allowed to stir at ambient temperature for approximately 16 hours after which the solvent is evaporated under reduced pressure, leaving a residue. This residue is poured into 200 mL of water, and the resulting mixture is extracted twice with ethyl acetate. The combined extracts are concentrated under reduced pressure, and the residue is passed through a column of silica gel, eluting with a heptane:ethyl acetate mixture. The product-containing fractions are combined, and the solvent is evaporated under reduced pressure leaving spiro[cyclopropane-1,2'-2,3-dihydro-7-nitro-3-benzofuranone] as a residue.
Step B Synthesis of spiro[cyclopropane-1,2'-2,3-dihydro-7-amino-3-benzofuranone]

By the method of Example 1, Step E, 3.69 g (0.018 mole) of spiro[cyclopropane-1,2'-2,3-dihydro-7-nitro-3-benzofuranone] and 5.0 g (0.090 mole) of powdered iron are reacted in 80 mL of glacial acetic acid and 10 mL of water, yielding spiro[cyclopropane-1,2'-7-amino-2,3-dihydro-3-benzofuranone].
Step C Synthesis of spiro[cyclopropane-1,2'-7-amino-4-chloro-2,3-dihydro-3-benzofuranone By the method of Example 3, Step C, 2.8 g (0.016 mole) of spiro[cyclopropane-1,2'-7-amino-2,3-dihydro-3-benzofuranone] is reacted with 2.14 g (0.016 mole) of N-chlorosuccinimide in 40 mL of N,N-dimethylformamide, yielding spiro[cyclopropane-1,2'-7-amino-4-chloro-2,3-dihydro-3-benzofuranone].
Step D Synthesis of spiro[cyclopropane-1,2'-4-chloro-2,3-dihydro benzofuran-3-on-7-yl]isocyanate By the method of Example 1, Step F, 2.93 g (0.014 mole) of spiro[cyclopropane-1,2'-7-amino-4-chloro-2,3-dihydro-3-benzofuranone] is reacted with 2.77 g (0.014 mole) of trichloromethyl chloroformate in 90 mL of toluene, yielding spiro[cyclopropane-1,2'-4-chloro-2,3-dihydrobenzofuran-3-on-7-yl]isocyanate.
Step E Synthesis of 3-spiro[cyclopropane-1,2'-4-chloro-2,3-dihydrobenzofuran-3-on-7-yl]-1-methyl-6-trifluoromethyluracil (Compound 31)

By the method of Example 1, Step G, 3.06 g (0.013 mole) of spiro[cyclopropane-1,2'-4-chlorobenzofuran-3-on-7-yl] isocyanate is reacted with 0.52 g (0.013 mole) of a 60% dispersion of sodium hydride in mineral oil and 2.35 g (0.013 mole) of ethyl 3-amino-4,4,4-trifluorocrotonate, yielding 3-spiro[cyclopropane-1,2'-4-chloro-2,3-dihydrobenzofuran-3-on-7-yl]-6-trifluoromethyluracil which is then reacted with 3.69 g (0.026 mole) of methyl iodide in the presence of 1.8 g (0.013 mole) of potassium carbonate, yielding 3-spiro[cyclopropane-1,2'-4-chloro-2,3-dihydrobenzofuran-3-on-7-yl]-1-methyl-6-trifluoromethyluracil (Compound 31).

EXAMPLE 9

SYNTHESIS OF 3-(4-CHLORO-2,3-DIHYDRO-2,2-DIMETHYL-3-THIOXOBENZOFURAN-7-YL)-1-METHYL-6-TRIFLUOROMETHYLURACIL (Compound 38)

Step A

Synthesis of 2,3-dihydro-2,2-dimethyl-7-nitrobenzofuran-3-thione

In a flask are placed 5.44 g (0.020 mole) of 3-bromo-2,3-dihydro-2,2-dimethyl-7-nitrobenzofuran (prepared by the method of Example 2, Step A) and 7.45 g (0.020 mole) of tetraethylammonium thiosulfate (prepared by the method of B. Hahn et al., *Liebigs Ann. Chem.* 1981, 10–19) in 100 mL of absolute ethanol. This mixture is heated at reflux for 24 hours after which the solvent is removed under reduced pressure, leaving a residue. This residue is taken up in 60 mL of diethyl ether which is then filtered to remove inorganic salts. Slowly, 20 mL of a 2N aqueous sodium hydroxide solution is added to the rapidly stirred filtrate. This mixture is stirred for 30 minutes at room temperature after which the aqueous phase is separated from the organic phase. The latter is washed with water, dried over anhydrous sodium sulfate, and filtered. The solvent is evaporated under reduced pressure, leaving a residue which is dissolved in methylene chloride. This solution is passed through a column of silica gel, eluting with methylene chloride. Product-containing fractions are combined, and the solvent is evaporated under reduced pressure, yielding 2,3-dihydro-2,2-dimethyl-7-nitrobenzofuran-3-thione.

Step B

Synthesis of 7-amino-2,3-dihydro-2,2-dimethylbenzofuran-3-thione

By the method of Example 1, Step E, 3.35 g (0.015 mole) of 2,3-dihydro-2,2-dimethyl-7-nitrobenzofuran-3-thione is reacted with 3.35 g (0.060 mole) of powdered iron in 50 mL of glacial acetic acid and 8 mL of water, yielding 7-amino-2,3-dihydro-2,2-dimethylbenzofuran-3-thione.

Step C

Synthesis of 7-amino-4-chloro-2,3-dihydro-2,2-dimethylbenzofuran-3-thione

By the method of Example 3, Step C, 2.51 g (0.013 mole) of 7-amino-2,3-dihydro-2,2-dimethylbenzofuran-3-thione is reacted with 1.74 g (0.013 mole) of N-chlorosuccinimide in 35 mL of N,N-dimethylformamide, yielding 7-amino-4-chloro-2,3-dihydro-2,2-dimethylbenzofuran-3-thione.

Step D

Synthesis of 4-chloro-2,3-dihydro-2,2-dimethyl-3-thioxobenzofuran-7-yl isocyanate By the method of Example 1, Step F, 2.51 g (0.011 mole) of 7-amino-4-chloro-2,3-dihydro-2,2-dimethylbenzofuran-3-thione is reacted with 2.18 g (0.011 mole) of trichloromethyl chloroformate in 65 mL of toluene, yielding 4-chloro-2,3-dihydro-2,2-dimethyl-3-thioxobenzofuran-7-yl isocyanate.

Step E

Synthesis of 3-(4-chloro-2,3-dihydro-2,2-dimethyl-3-thioxobenzofuran-7-yl)-1-methyl-6-trifluoromethyluracil By the method of Example 1, Step G, 2.15 g (0.010 mole) of 4-chloro-2,3-dihydro-2,2-dimethyl-3-thioxobenzofuran-7-yl isocyanate is reacted with 0.40 g (0.010 mole) of sodium hydride and 1.83 g (0.010 mole) of ethyl 3-amino-4,4,4-trifluorocrotonate, yielding 3-(4-chloro-2,3-dihydro-2,2-dimethyl-3-thioxobenzofuran-7-yl)-6-trifluoromethyluracil. This product is further reacted with 1.38 g (0.010 mole) of potassium carbonate and 2.80 g (0.020 mole) of methyl iodide, yielding 3-(4-chloro-2,3-dihydro-2,2-dimethyl-3-thioxobenzofuran-7-yl)-1-methyl-6-trifluoromethyluracil (Compound 38).

EXAMPLE 10

SYNTHESIS OF 3-(4-CHLORO-6-FLUORO-2,3-DIHYDRO-2,2-DIMETHYL-3-HYDROXYBENZOFURAN-7-YL)-1-METHYL-6-TRIFLUOROMETHYLURACIL (Compound 39)

By the method of Example 3, Step A, 19.6 grams (0.05 mole) of 3-(4-chloro-6-fluoro-2,3-dihydro-2,2-dimethylbenzofuran-7-yl)-1-methyl-6-trifluoromethyluracil (Compound 4) was reacted with 27.0 grams (0.10 mole) of potassium persulfate and 13.0 grams (0.05 mole) of copper(II) sulfate pentahydrate in 150 mL of acetonitrile and 150 mL of water. The reaction mixture, containing both 3-(4-chloro-6-fluoro-2,3-dihydro-2,2-dimethyl-3-hydroxybenzofuran-7-yl)-1-methyl-6-trifluoromethyluracil and 3-(4-chloro-6-fluoro-2,3-dihydro-2,2-dimethylbenzofuran-3-on-7-yl)-1-methyl-6-trifluoromethyluracil, was extracted with diethyl ether and the extract dried with magnesium sulfate and filtered. The filtrate was concentrated under reduced pressure to a residue, which was subjected to column chromatography on silica gel, with methylene chloride as the eluant. The appropriate product-containing fractions were combined and concentrated under reduced pressure, yielding 12.9 grams of 3-(4-chloro-6-fluoro-2,3-dihydro-2,2-dimethyl-3-hydroxybenzofuran-7-yl)-1-methyl-6-trifluoromethyluracil, mp 82°–83° C. The NMR spectrum was consistent with the proposed structure.

EXAMPLE 11

SYNTHESIS OF 3-(5-CHLORO-3,4-DIHYDRO-7-FLUORO-2H-1-BENZOPYRAN-8-YL)-1-METHYL-6-TRIFLUOROMETHYLURACIL (Compound 40)

Step A

Synthesis of 3-(3-fluorophenoxy)propanol as an intermediate

A stirred mixture of 24.3 grams (0.174 mole) of 3-bromopropanol, 20.6 grams (0.180 mole) of 3-fluorophenol, and 37.0 grams (0.270 mole) of potassium carbonate in 300 mL of acetone was heated at reflux for about 18 hours. The reaction mixture was then cooled and concentrated under reduced pressure to a residue, which was stirred with water and extracted with diethyl ether. The ether extract was washed with an aqueous 10% sodium hydroxide solution and then with water. The organic layer was dried with magnesium sulfate and filtered. The filtrate was concentrated under reduced pressure, yielding 24.5 grams of 3-(3-fluorophenoxy)propanol. The NMR spectrum was consistent with the proposed structure.

Step B

Synthesis of 3-(3-fluorophenoxy)propanecarboxylic acid as an intermediate

To a stirred solution of 12.0 grams (0.071 mole) of 3-(3-fluorophenoxy)propanol in 150 mL of acetone Jones reagent (a mixture of chromic acid and sulfuric acid in water) was added dropwise until an orange color persisted in the reaction mixture. Isopropanol was then added dropwise until the color of the reaction mixture became blue/green. The reaction mixture was then slurried with silica gel and filtered. The filter cake was washed with ethyl acetate. The combined wash and filtrate were concentrated under reduced pressure to a residue, which was dissolved in methylene chloride and washed with water. The organic layer was dried with magnesium sulfate and filtered. The filtrate was concentrated under reduced pressure, yielding 12.8 grams of 3-(3-fluorophenoxy)propanecarboxylic acid. The NMR spectrum was consistent with the proposed structure.

Step C

Synthesis of 3,4-dihydro-7-fluoro-2H-1-benzopyran-4-one as an intermediate

To a stirred solution of 2.0 grams (0.011 mole) of 3-(3-fluorophenoxy)propanecarboxylic acid in 50 mL of methylene chloride 3.6 grams (0.017 mole) of phosphorous pentachloride was added portionwise during a five minute period. Upon completion of the addition, the reaction mixture was cooled in an ice-water bath, and 4.4 grams (0.033 mole) of aluminium chloride was added portionwise during a five minute period. Upon completion of the addition, the reaction mixture was allowed to warm to ambient temperature where it stirred for two hours. The reaction mixture was poured into ice, extracted with diethyl ether, and the extract washed first with water and then with an aqueous 10% sodium hydroxide solution. The organic layer was dried with magnesium sulfate and filtered. The filtrate was concentrated under reduced pressure to a residue, which was subjected to column chromatography on silica gel, with 1:2 and 1:1 methylene chloride:hexane as eluants. The product-containing fractions were combined and concentrated under reduced pressure, yielding 0.9 gram of 3,4-dihydro-7-fluoro-2H-1-benzopyran-4-one. The NMR spectrum was consistent with the proposed structure. This reaction was repeated several times.

Step D

Synthesis of 3,4-dihydro-7-fluoro-4-hydroxy-2H-1-benzopyran as an intermediate To a stirred solution of 5.0 grams (0.03 mole) of 3,4-dihydro-7-fluoro-2H-1-benzopyran-4-one in 100 mL of methanol was added portionwise 3.4 grams (0.09 mole) of sodium borohydride during a one hour period, after which the reaction mixture was stirred for about 18 hours. The reaction mixture was then concentrated under reduced pressure to a residue, which was slurried in water and extracted with methylene chloride. The extract was dried with magnesium sulfate and filtered. The filtrate was concentrated under reduced pressure to a residue, which was subjected to column chromatography on silica gel, with 1:4 ethyl acetate:hexane as the eluant. The product-containing fractions were combined and concentrated under reduce pressure, yielding 4.4 grams of 3,4-dihydro-7-fluoro-4-hydroxy-2H-1-benzopyran. The NMR spectrum was consistent with the proposed structure. This reaction was repeated several times.

Step E

Synthesis of 7-fluoro-2H-1-benzopyran as an intermediate

A reaction vessel charged with 0.5 gram (0.03 mole) of 3,4-dihydro-7-fluoro-4-hydroxy-2H-1-benzopyran and 0.02 gram (catalyst) of p-toluenesulfonic acid in 50 mL of toluene was fitted with a Soxhlet extractor containing molecular sieves (3–4 angstrom). The stirred contents of the reaction vessel was heated at reflux for 90 minutes, during which time the water by-product was collected on the molecular sieves. The reaction mixture was combined with the reaction mixture of another preparation of this compound and concentrated under reduced pressure to a residue. The residue was subjected to column chromatography on silica gel, with 1:9 ethyl acetate:hexane as the eluant. The product-containing fractions were combined and concentrated under reduced pressure, yielding 0.6 gram of 7-fluoro-2H-1-benzopyran. The NMR spectrum was consistent with the proposed structure. This reaction was repeated several times.

Step F

Synthesis of 3,4-dihydro-7-fluoro-2H-1-benzopyran as an intermediate

A mixture of 12.1 grams (0.081 mole) of 7-fluoro-2H-1-benzopyran and a catalytic amount of 5% palladium on carbon in about 200 mL of ethanol was shaken in a Parr hydrogenator until the theoretical amount of hydrogen gas was taken up. After this time the reaction mixture was filtered and concentrated under reduced pressure, yielding 10.5 grams of 3,4-dihydro-7-fluoro-2H-1-benzopyran. The NMR spectrum was consistent with the proposed structure.

Step G

Synthesis of 3,4-dihydro-7-fluoro-2H-1-benzopyran-8-ylcarboxylic acid as an intermediate A stirred solution of 30.4 mL (0.076 mole) of n-butyllithium (2.5M in hexanes) in 200 mL of tetrahydrofuran was cooled to −78 °C., and 10.5 grams (0.069 mole) of 3,4-dihydro-7-fluoro-2H-1-benzopyran was added portionwise. Upon completion of the addition, the reaction mixture was maintained at −78° C. for 30 minutes. The reaction mixture was then exposed to a carbon dioxide atmosphere for 18 hours. The reaction mixture was then stirred with diethyl ether and extracted with an aqueous 5% sodium hydroxide solution. The basic layer was washed with diethyl ether, made acidic with concentrated hydrochloric acid, and then extracted with diethyl ether. The extract was dried with magnesium sulfate and filtered. The filtrate was concentrated under reduced pressure, yielding 10.2 grams of 3,4-dihydro-7-fluoro-2H-1-benzopyran-8-ylcarboxylic acid. The NMR spectrum was consistent with the proposed structure.

Step H

Synthesis of 1,1-dimethylethyl N-(3,4-dihydro-7-fluoro-2H-1-benzofuran-8-yl)carbamate as an intermediate A stirred solution of 10.2 grams (0.052 mole) of 3,4-dihydro-7-fluoro-2H-1-benzopyran-8-ylcarboxylic acid, 14.3 grams (0.052 mole) of diphenylphosphoryl azide, and 5.3 grams (0.052 mole) of triethylamine in 150 mL of tert.-butanol was heated at reflux for about 18 hours. The reaction mixture was then concentrated under reduced pressure to a residue, which was subjected to column chromatography on silica gel, with 1:4 ethyl acetate:hexane as the eluant. The product-containing fractions were combined and concentrated under reduced pressure, yielding 6.1 grams of 1,1-dimethylethyl N-(3,4-dihydro-7-fluoro-2H-1-benzopyran-8-yl)carbamate. The NMR spectrum was consistent with the proposed structure.

Step I

Synthesis of 8-amino-3,4-dihydro-7-fluoro-2H-1-benzopyran as an intermediate Trifluoroacetic acid, 50 mL, was stirred and cooled in an ice-water bath, and 6.1 grams (0.023 mole) of 1,1-dimethylethyl N-(3,4-dihydro-7-fluoro-2H-1-benzopyran-8-yl)carbamate was added portionwise. Upon completion of the addition, the reaction mixture was stirred for one hour, then stirred with water and diethyl ether and neutralized with solid sodium bicarbonate. The water layer was separated and extracted with diethyl ether. The extract was combined with the organic layer, and the combination was washed with water. The organic layer was dried with magnesium sulfate and filtered. The filtrate was concentrated under reduced pressure, yielding 3.7 grams of 8-amino-3,4-dihydro-7-fluoro-2H-1-benzopyran. The NMR spectrum was consistent with the proposed structure.

Step J

Synthesis of 8-amino-5-chloro-3,4-dihydro-7-fluoro-2H-1-benzopyran as an intermediate To a stirred solution of 3.7 grams (0.022 mole) of 8-amino-3,4-dihydro-7-fluoro-2H-1-benzopyran in 50 mL of N,N-dimethylformamide was added dropwise a solution of 3.0 grams (0.022 mole) of N-chlorosuccinimide in about 20 mL of N,N-dimethylformamide. Upon completion of the addition, the reaction mixture was stirred for about 90 minutes and poured into an aqueous 10% lithium chloride solution. The mixture was extracted with diethyl ether. An insoluble material was collected by filtration and dissolved in methylene chloride. The methylene chloride solution was washed with water and dried with magnesium sulfate. The mixture was filtered, and the filtrate was set aside. The diethyl ether extract was washed with an aqueous 10% lithium chloride solution and dried with magnesium sulfate. The mixture was filtered, and the filtrate was combined with the methylene chloride filtrate. The combination was concentrated under reduced pressure to a residue, which was subjected to column chromatography on silica gel with 1:4 ethyl acetate:hexane as the eluant. The product-containing fractions were combined and concentrated under reduced pressure, yielding 2.2 grams of 8-amino-5-chloro-3,4-dihydro-7-fluoro-2H-1-benzopyran. The NMR spectrum was consistent with the proposed structure.

Step K

Synthesis of 5-chloro-3,4-dihydro-7-fluoro-2H-1-benzopyran-8-yl isocyanate as an intermediate By the method of Example 1, Step F, 2.2 grams (0.011 mole) of 8-amino-5-chloro-3,4-dihydro-7-fluoro-2H-1-benzopyran and 2.2 grams (0.011 mole) of trichloromethyl chloroformate were reacted in 50 mL of toluene, yielding about 2.5 grams of 5-chloro-3,4-dihydro-7-fluoro-2H-1-benzopyran-8-yl isocyanate. The product was taken to the next step without further characterization.

Step L

Synthesis of 3-(5-chloro-3,4-dihydro-7-fluoro-2H-1-benzopyran-8-yl)-6-trifluoromethyluracil as an intermediate By a method analogous to that of Example 1, Step G, 2.5 grams (0.011 mole) of 5-chloro-3,4-dihydro-7-fluoro-2H-1-benzopyran-8-yl isocyanate was reacted with ethyl 3-amino-4,4,4-trifluorocrotonate and 0.66 gram (0.012 mole) of sodium hydride (60% in mineral oil) in 150 mL of tetrahydrofuran. The crude reaction product was subjected to column chromatography on silica gel, with 1:2 ethyl acetate:hexane as the eluant. The product-containing fractions were combined and concentrated under reduced pressure, yielding 3.0 grams of 3-(5-chloro-3,4-dihydro-7-fluoro-2H-1-benzopyran-8-yl)-6-trifluoromethyluracil. The NMR spectrum was consistent with the proposed structure.

Step M

Synthesis of 3-(5-chloro-3,4-dihydro-7-fluoro-2H-1-benzopyran-8-yl)-1-methyl-6-trifluoromethyluracil (Compound 40)

By a method analogous to that of Example 1, Step G, 2.9 grams (0.008 mole) of 3-(5-chloro-3,4-dihydro-7-fluoro-2H-1-benzopyran-8-yl)-6-trifluoromethyluracil was reacted with 2.2 grams (0.016 mole) of potassium carbonate and 1.7 grams (0.012 mole) of methyl iodide in 50 mL of N,N-dimethylformamide. The crude reaction product was subjected to column chromatography on silica gel, with 1:9 to 1:4 ethyl acetate:hexane as eluants. The product-containing fractions were combined and concentrated under reduced pressure, yielding 2.8 grams of 3-(5-chloro-3,4-dihydro-7-fluoro-2H-1-benzopyran-8-yl)-1-methyl-6-trifluoromethyluracil, mp 141°–145° C. The NMR spectrum was consistent with the proposed structure.

EXAMPLE 12

SYNTHESIS OF 3-(5-CHLORO-3,4-DIHYDRO-7-FLUORO-2H-1-BENZOPYRAN-4-ON-8-YL)-1-METHYL-6-TRIFLUOROMETHYLURACIL (Compound 46)

By the method of Example 3, Step A, 0.5 gram (0.0013 mole) of 3-(5-chloro-3,4-dihydro-7-fluoro-2H-1-benzopyran-8-yl)-1-methyl-6-trifluoromethyluracil was reacted with 1.1 grams (0.0040 mole) of potassium persulfate and 0.3 gram (0.0013 mole) of copper(11) sulfate pentahydrate in 30 mL of acetonitrile and 30 mL of water, yielding 0.5 gram of 3-(5-chloro-3,4-dihydro-7-fluoro-2H-1-benzopyran-3-on-8-yl)-1-methyl-6-trifluoromethyluracil. The NMR spectrum was consistent with the proposed structure. This product was combined with another run of this reaction. The combined runs were subjected to column chromatography on silica gel, with 1:4 to 1:2 ethyl acetate:hexane as eluants. The product-containing fractions were combined and concentrated under reduced pressure, yielding 0.8 gram of 3-(5-chloro-3,4-dihydro-7-fluoro-2H-1-benzopyran-4-on-8-yl)-1-methyl-6-trifluoromethyluracil. The NMR spectrum was consistent with the proposed structure.

EXAMPLE 13

SYNTHESIS OF
3-(5-CHLORO-2,2-DIMETHYL-7-FLUORO-
2H-1-BENZOPYRAN-8-YL)-1-METHYL-
6-TRIFLUOROMETHYLURACIL (Compound 50)

Step A

Synthesis of
3-(2-cyano-3-fluorophenoxy)-3-methyl-1-butyne as
an intermediate

To a stirred solution of 108.3 grams (0.78 mole) of 2,6-difluorobenzonitrile and 78.2 grams (0.93 mole) of 2-methyl-3-butyn-2-ol in 800 mL of dimethyl sulfoxide 65.5 grams (1.17 moles) of potassium hydroxide was added portionwise during a 20 minute period. Upon completion of the addition, the reaction mixture was stirred at ambient temperature for about 18 hours, after which the reaction mixture was poured into ice-water and extracted with diethyl ether. The extract was washed with water and dried with magnesium sulfate. The mixture was filtered and the filtrate concentrated under reduced pressure, yielding 75.3 grams of 3-(2-cyano-3-fluoro-phenoxy)- 3-methyl-1-butyne. The NMR spectrum was consistent with the proposed structure.
Step B Synthesis of
8-cyano-2,2-dimethyl-7-fluoro-2H-1-benzopyran One thousand mL of stirred, 1,2-dichlorobenzene was heated to 180° C., and a solution of 75.0 grams (0.37 mole) of 3-(2-cyano-3-fluorophenoxy)-3-methyl-1-butyne in 100 mL of 1,2-dichlorobenzene was added dropwise. Upon completion of the addition, the reaction mixture was stirred at 180° C. for one hour, after which the reaction mixture was cooled and subjected to column chromatography on silica gel. The 1,2-dichlorobenzene solvent was separated by elution with hexane. The product was removed from the column by elution with methylene chloride. The product-containing fractions were combined and concentrated under reduced pressure, yielding 37.0 of 8-cyano-2,2-dimethyl-7-fluoro-2H-1-benzopyran, mp 99°–101° C. The NMR spectrum was consistent with the proposed structure.
Step C Synthesis of
2,2-dimethyl-7-fluoro-2H-1-benzopyran-
8-yl-carboxamide as an intermediate A stirred solution of 5.0 grams (0.025 mole) of 8-cyano-2,2-dimethyl-7-fluoro-2H-1-benzopyran and 5.1 grams (0.091 mole) of potassium hydroxide in 60 mL of tert.-butanol was maintained at reflux for one hour and then poured into an aqueous solution saturated with sodium chloride. The mixture was extracted with ethyl acetate, and the extract was washed with an aqueous solution saturated with sodium chloride. The organic layer was dried with magnesium sulfate and filtered. The filtrate was concentrated under reduced pressure, yielding 2.7 grams of 2,2-dimethyl-7-fluoro-2H-1-benzopyran-8-ylcarboxamide. The NMR spectrum was consistent with the proposed structure.
Step D Synthesis of
8-amino-2,2-dimethyl-7-fluoro-2H-1-benzopyran as
an intermediate Stirred CLOROX® bleach, 25.9 grams (5.25% sodium hypochlorite-0.018 mole), was cooled in an ice-water bath, and a solution of 2.0 grams (0.049 mole) of sodium hydroxide in 30 mL of water was added dropwise. The reaction mixture was maintained at about 0° C., and a solution of 2.7 grams (0.012 mole) of 2,2-dimethyl-7-fluoro-2H-1-benzopyran-8-ylcarboxamide in 30 mL of dioxane was added dropwise. Upon completion of the addition, the reaction mixture was stirred at 0° C. for one hour, then it was warmed to 70° C., where it stirred for an additional one hour. The reaction mixture was allowed to cool to ambient temperature as it stirred for about 18 hours. The reaction mixture was then extracted with ethyl acetate, and the extract was washed with an aqueous solution saturated with sodium chloride. The organic layer was dried with magnesium sulfate and filtered. The filtrate was concentrated under reduced pressure, yielding 2.0 grams of 8-amino-2,2-dimethyl-7-fluoro-2H-1-benzopyran. The NMR spectrum was consistent with the proposed structure.
Step E Synthesis of
8-amino-5-chloro-2,2-dimethyl-7-fluoro-
2H-1-benzopyran as an intermediate By a method analogous to that of Example 11, Step J, 1.5 grams (0.0008 mole) of 8-amino-2,2-dimethyl-7-fluoro-2H-1-benzopyran was reacted with 1.1 grams (0.008 mole) of N-chlorosuccinimide in 50 mL of N,N-dimethylformamide. The crude reaction product was purified with column chromatography on silica gel, with hexane and 1:1 methylene chloride:hexane hexane as the eluants. The product-containing fractions were combined and concentrated under reduced pressure, yielding 0.6 gram of 8-amino-5-chloro-2, 2-dimethyl-7-fluoro-2H-1-benzopyran. The NMR spectrum was consistent with the proposed structure.
Step F Synthesis of
5-chloro-2,2-dimethyl-7-fluoro-2H-1-benzopyran-8-yl
isocyanate as an intermediate By the method of Example 1, Step F, 1.3 grams (0.005 mole) of 8-amino-5-chloro-2,2-dimethyl-7-fluoro-2H-1-benzopyran and 1.1 grams (0.005 mole) of trichloromethyl chloroformate were reacted in 50 mL of toluene, yielding about 1.4 grams of 5-chloro-2,2-dimethyl-7-fluoro-2H-1-benzopyran-8-yl isocyanate. The product was taken to the next step without further characterization.
Step G Synthesis of
3-(5-chloro-2,2-dimethyl-7-fluoro-2H-1-
benzopyran-8-yl)-1-methyl-6-trifluoromethyluracil
(Compound 50)

By the method of Example 1, Step G, 1.4 grams (0.005 mole) of 5-chloro-2,2-dimethyl-7-fluoro-2H-1-benzopyran-8-yl isocyanate was reacted with 0.3 gram (0.008 mole) of sodium hydride and 1.1 grams (0.006 mole) of ethyl 3-amino-4,4,4-trifluorocrotonate in 100 mL of tetrahydrofuran. Subsequently, 1.6 grams (0.011 mole) of methyl iodide and 1.5 grams (0.011 mole) of potassium carbonate were reacted with the product of the first reaction. The crude reaction product was purified by column chromatography on silica gel, with 1:9 methylene chloride:hexane and pure methylene chloride as eluants. The product-containing fractions were combined and concentrated under reduced pressure, yielding 1.5 grams of 3-(5-chloro-2,2-dimethyl-7-fluoro-2H-1-benzopyran-8-yl)-1-methyl-6-trifluoromethyluracil. The NMR spectrum was consistent with the proposed structure.

EXAMPLE 14

SYNTHESIS OF
3-(5-CHLORO-3,4-DIHYDRO-2,2-DIMETHYL-7-FLUORO-2H-1-BENZOPYRAN-4-ON-8-YL)-1-METHYL-6-TRIFLUOROMETHYLURACIL
(Compound 47)

Step A

Synthesis of
8-amino-3,4-dihydro-2,2-dimethyl-7-fluoro-2H-1-benzopyran as an intermediate By the method of Example 11, Step F, 7.3 grams (0.038 mole) of 8-amino-2,2-dimethyl-7-fluoro-2H-1-benzopyran (prepared in Example 13, Step D) was hydrogenated in the presence of 5% palladium on carbon in about 150 mL of ethanol. The yield of 8-amino-3,4-dihydro-2,2-dimethyl-7-fluoro-2H-1-benzopyran was 6.7 grams. The NMR spectrum was consistent with the proposed structure.

Step B

Synthesis of
8-amino-5-chloro-3,4-dihydro-2,2-dimethyl-7-fluoro-2H-1-benzopyran as an intermediate By a method analogous to that of Example 11, Step J, 6.7 grams (0.034 mole) of 8-amino-3,4-dihydro-2,2-dimethyl-7-fluoro-2H-1-benzopyran was reacted with 4.6 grams (0.035 mole) of N-chlorosuccinimide in 100 mL of N,N-dimethylformamide. The crude reaction product was purified with column chromatography on silica gel, with hexane and 1:4 methylene chloride:hexane as the eluants. The product-containing fractions were combined and concentrated under reduced pressure, yielding 4.0 grams of 8-amino-5-chloro-3,4-dihydro-2,2-dimethyl-7-fluoro-2H-1-benzopyran. The NMR spectrum was consistent with the proposed structure.

Step C

Synthesis of
5-chloro-3,4-dihydro-2,2-dimethyl-7-fluoro-2H-1-benzopyran-8-yl isocyanate as an intermediate By the method of Example 1, Step F, 3.6 grams (0.016 mole) of 8-amino-5-chloro-3,4-dihydro-2,2-dimethyl-7-fluoro-2H-1-benzopyran and 3.1 grams (0.016 mole) of trichloromethyl chloroformate were reacted in 100 mL of toluene, yielding about 4.0 grams of 5-chloro-3,4-dihydro-2,2-dimethyl-7-fluoro-2H-1-benzopyran-8-yl isocyanate. The product was taken to the next step without further characterization.

Step D

Synthesis of
3-(5-chloro-3,4-dihydro-2,2-dimethyl-7-fluoro-2H-1-benzopyran-8-yl)-1-methyl-6-trifluoromethyluracil
as an intermediate By the method of Example 1, Step G, 4.0 grams (0.016 mole) of 5-chloro-3,4-dihydro-2,2-dimethyl-7-fluoro-2H-1-benzopyran-8-yl isocyanate was reacted with 1.0 gram (0.023 mole) of sodium hydride and 3.0 grams (0.017 mole) of ethyl 3-amino-4,4,4-trifluorocrotonate in 150 mL of tetrahydrofuran. Subsequently, 4.5 grams (0.032 mole) of methyl iodide and 4.4 grams (0.032 mole) of potassium carbonate were reacted with the product of the first reaction, yielding 2.4 grams of 3-(5-chloro-3,4-dihydro-2,2-dimethyl-7-fluoro-2H-1-benzopyran-8-yl)-1-methyl-6-trifluoromethyluracil, mp 132°–135° C. The NMR spectrum was consistent with the proposed structure.

Step E

Synthesis of
3-(5-chloro-3,4-dihydro-2,2-dimethyl-7-fluoro-2H-1-benzopyran-4-on-8-yl)-1-methyl-6-trifluoromethyluracil (Compound 47)

By the method of Example 3, Step A, 1.8 grams (0.004 mole) of 3-(5-chloro-3,4-dihydro-2,2-dimethyl-7-fluoro-2H-1-benzopyran-8-yl)-1-methyl-6-trifluoromethyluracil was reacted with 3.5 grams (0.013 mole) of potassium persulfate and 1.1 grams (0.004 mole) of copper(II) sulfate pentahydrate in 30 mL of acetonitrile and 30 mL of water. The crude reaction mixture was subjected to column chromatography on silica gel, with 1:4 ethyl acetate:hexane as the eluant. The product-containing fractions were combined and concentrated under reduced pressure, yielding 0.8 gram of 3-(5-chloro-3,4-dihydro- 2,2-dimethyl-7-fluoro-2H-1-benzopyran-4-on-8-yl)-1-methyl-6-trifluoromethyluracil. The NMR spectrum was consistent with the proposed structure.

EXAMPLE 15

SYNTHESIS OF
1-AMINO-3-(4-CHLORO-2,3-DIHYDRO-2,2-DIMETHYLBENZOFURAN-7-YL)-6-TRIFLUOROMETHYLURACIL (Compound 58)

Step A

Synthesis of 1,1-dimethylethyl
N-(2,4,6-trimethylphenylsulfonyloxy)carbamate as an intermediate A stirred solution of 25.0 grams (0.114 mole) of 2,4,6-trimethylbenzenesulfonyl chloride and 15.3 grams (0.114 mole) of 1,1-dimethylethyl N-hydroxycarbamate in 350 mL of diethyl ether was cooled in an ice-water bath, and 11.4 grams (0.114 mole) of triethylamine was added dropwise. Upon completion of the addition, the reaction mixture was allowed to warm to ambient temperature as it stirred for about 18 hours. The reaction mixture was then filtered, and the filtrate was concentrated under reduced pressure to a residue, which was slurried with toluene and petroleum ether. The resultant solid was collected by filtration, yielding 25.0 grams of 1,1-dimethylethyl N-(2,4,6-trimethylphenylsulfonyloxy)carbamate. The NMR spectrum was consistent with the proposed structure.

Step B

Synthesis of 1-aminooxysulfonyl-2,4,6-trimethylbenzene as an intermediate

Trifluoroacetic acid, 80.0 mL, was stirred and cooled in an ice-water bath, and 25.0 grams (0,079 mole) of 1,1-dimethylethyl N-(2,4,6-trimethylphenylsulfonyloxy)carbamate was added portionwise. Upon completion of the addition, the reaction mixture was stirred for 90 minutes, then poured into ice-water The resultant solid was collected by filtration and dissolved in diethyl ether. The solution was then dried with magnesium sulfate and filtered. The solid product was precipitated from the filtrate by the addition of petroleum ether. The solid was collected by filtration, yielding 14.4 grams of 1-aminooxysulfonyl-2,4,6-trimethylbenzene. The NMR spectrum was consistent with the proposed structure.

Step C

Synthesis of 1-amino-3-(4-chloro-2,3-dihydro-2,2-dimethylbenzofuran-7-yl)-6-trifluoromethyluracil (Compound 58)

A solution of 1.0 gram (0.003 mole) of 3-(4-chloro-2,3-dihydro-2,2-dimethylbenzofuran-7-yl)-6-trifluoromethyluracil (prepared in a manner analogous to that of Example 1, Step G, except that methyl iodide and potassium carbonate were not used) in 30 mL of tetrahydrofuran was stirred, and 0.5 gram (0.003 mole) of potassium carbonate, then 0.7 gram (0.003 mole) of 1-aminooxysulfonyl-2,4,6-trimethylbenzene were added. Upon completion of the addition, the reaction mixture was stirred for one hour and then diluted with water and extracted with three portions of ethyl acetate. The combined extracts were dried with magnesium sulfate and filtered. The filtrate was concentrated under reduced pressure to a residue, which was subjected to column chromatography on silica gel, with 1:4 ethyl acetate:heptane as the eluant. The product-containing fractions were combined and concentrated, yielding 1.0 gram of 1-amino-3-(4-chloro-2,3-dihydro-2,2-dimethylbenzofuran- 7-yl)-6-trifluoromethyluracil. The NMR spectrum was consistent with the proposed structure.

EXAMPLE 16

SYNTHESIS OF 3-(4-BROMO-2,3-DIHYDRO-2-METHOXYCARBONYL-2-METHYLBENZOFURAN-3-ON-7-YL)-1-METHYL-6-TRIFLUOROMETHYLURACIL (Compound 56)

Step A

Synthesis of 5-chloro-2-ethoxycarbonyl-2,3-dihydro-3-hydroxy-2-methylbenzofuran as an intermediate A stirred solution of 30.0 grams (0.192 mole) of 5-chloro-2-hydroxy-benzaldehyde, 31.4 grams (0.230 mole) ethyl 2-chloropropionate, and 31.8 grams (0.230 mole) of potassium carbonate in 200 mL of N,N-dimethylformamide was heated at 60°–70° C. for about 18 hours. The reaction mixture was cooled, diluted with 200 mL of aqueous 10% lithium chloride solution, and then extracted with two portions of ethyl acetate. The combined extracts were washed with 100 mL of aqueous 10% lithium chloride solution and dried with magnesium sulfate. The mixture was filtered, and the filtrate was concentrated under reduced pressure to a residual oil. Infrared spectroscopy indicated that the residual oil was an intermediate product that had not closed to form the benzofuran ring. A small sample (0.6 gram) was removed for other experiments. The remainder of the residual oil was dissolved in 100 mL of N,N-dimethylformamide, and 26.5 grams (0.182 mole) of potassium carbonate was added. The stirred mixture was warmed to 70 °C., where it stirred for about 18 hours. The reaction mixture was processed as described above, yielding about 45 grams of crude product. The product was subjected to column chromatography on silica gel, with 1.5:8.5 ethyl acetate:heptane as the eluant. The product-containing fractions were combined and concentrated under reduced pressure, yielding 28.3 grams of 5-chloro-2-ethoxycarbonyl-2,3-dihydro-3-hydroxy-2-methylbenzofuran. The NMR spectrum was consistent with the proposed structure.

Step B

Synthesis of 3,5-dichloro-2-ethoxycarbonyl-2,3-dihydro-2-methylbenzofuran as an intermediate A solution of 27.9 grams (0.109 mole) of 5-chloro-2-ethoxycarbonyl-2,3-dihydro-3-hydroxy-2-methylbenzofuran in 200 mL of methylene chloride was stirred, and four drops of pyridine was added. The reaction mixture was cooled in an ice-water bath, and 19.4 grams (0.163 mole) of thionyl chloride was added dropwise. The reaction mixture was then stirred for about 30 minutes at the ice-water bath temperature, and allowed to warm to ambient temperature, where it stirred for about 18 hours. After this time the reaction mixture was concentrated under reduced pressure to a residue, which was diluted with water and ethyl acetate, and washed with a solution saturated with sodium bicarbonate. The aqueous layer was separated and washed with two portions of ethyl acetate. The organic layer and the ethyl acetate washes were combined and dried with magnesium sulfate. The mixture was filtered and the filtrate concentrated under reduced pressure to a residual oil, which was subjected to column chromatography on silica gel, with 1:9 ethyl acetate:heptane as the eluant. The product-containing fractions were combined and concentrated under reduced pressure, yielding 27.3 grams of 3,5-dichloro-2-ethoxycarbonyl-2,3-dihydro-2-methylbenzofuran. The NMR spectrum was consistent with the proposed structure.

Step C

Synthesis of 5-chloro-2-ethoxycarbonyl-2,3-dihydro-2-methylbenzofuran as an intermediate By the method of Example 11, Step F, 27.2 grams (0.099 mole) of 3,5-dichloro-2-ethoxycarbonyl-2,3-dihydro-2-methylbenzofuran was hydrogenated in the presence of 10% palladium on carbon in about 225 mL of ethanol. The yield of 5-chloro-2-ethoxycarbonyl-2,3-dihydro-2-methylbenzofuran was 18.7 grams. The NMR spectrum was consistent with the proposed structure.

Step D

Synthesis of 5-chloro-2-ethoxycarbonyl-2,3-dihydro-2-methyl-7-nitrobenzofuran as an intermediate Stirred concentrated sulfuric acid, 50 mL, was cooled in an ice-water bath, and 9.0 grams (0.037 mole) of 5-chloro-2-ethoxycarbonyl-2,3-dihydro-2-methylbenzofuran was added. To this solution was added dropwise a solution of 2.6 grams (0.041 mole) of 90% nitric acid in 2 mL of concentrated sulfuric acid, while maintaining the reaction mixture temperature at 10°–16° C. Upon completion of the addition, the reaction mixture was stirred at the ice-water bath temperature for 30 minutes, then allowed to warm to ambient temperature where it stirred for one hour. The reaction mixture was poured into ice and neutralized with sodium bicarbonate and extracted with three portions of methylene chloride. The combined extracts were dried with magnesium sulfate and filtered. The filtrate was concentrated under reduced pressure to a residual oil. The oil was subjected to column chromatography on silica gel, with 3:7 ethyl acetate:heptane as the eluant. The product-containing fractions were combined and concentrated under reduced pressure, yielding 4.0 grams of 5-chloro-2-ethoxycarbonyl-2,3-dihydro-2-methyl-7-nitrobenzofuran, mp 69°–72.5° C. The NMR spectrum was consistent with the proposed structure. This reaction was repeated.

Step E

Synthesis of
7-amino-2-ethoxycarbonyl-2,3-dihydro-
2-methylbenzofuran as an intermediate By the method of Example 11, Step F, 3.1 grams (0.011 mole) of 5-chloro-2-ethoxycarbonyl-2,3-dihydro-2-methyl-7-nitrobenzofuran was hydrogenated in the presence of 10% palladium on carbon in about 150 mL of ethanol. The yield of 7-amino-2-ethoxycarbonyl-2,3-dihydro-2-methylbenzofuran was 1.2 grams. The NMR spectrum was consistent with the proposed structure.

Step F

Synthesis of
7-amino-4-bromo-2-ethoxycarbonyl-2,3-dihydro-
2-methylbenzofuran as an intermediate A stirred solution of 1.2 grams (0.005 mole) of 7-amino-2-ethoxycarbonyl-2,3-dihydro-2-methylbenzofuran in 50 mL of N,N-dimethylformamide was cooled in an ice-water bath, and 1.0 gram (0.005 mole) of N-bromosuccinimide was added. Upon completion of the addition, the reaction mixture was stirred at the ice-water bath temperature for about one hour and then allowed to warm to ambient temperature, where it stirred for about 18 hours. The reaction mixture was diluted with an aqueous 10% lithium chloride solution, and extracted with two portions of ethyl acetate. The combined extracts were washed with 50 mL of an aqueous 10% lithium chloride solution and dried with magnesium sulfate. The mixture was filtered, and the filtrate was concentrated under reduced pressure to a residual oil, which was subjected to column chromatography on silica gel, with 1:4 ethyl acetate:heptane as the eluant. The product-containing fractions were combined and concentrated under reduced pressure, yielding 1.6 grams of 7-amino-4-bromo-2-ethoxycarbonyl-2,3-dihydro-2-methylbenzofuran. The NMR spectrum was consistent with the proposed structure.

Step G

Synthesis of
4-bromo-2-ethoxycarbonyl-2,3-dihydro-2-
methylbenzofuran-7-yl isocyanate as an
intermediate By the method of Example 1, Step F, 1.6 grams (0.005 mole) of 7-amino-4-bromo-2-ethoxycarbonyl-2,3-dihydro-2-methylbenzofuran and 1.0 gram (0.005 mole) of trichloromethyl chloroformate were reacted in 60 mL of toluene, yielding about 1.7 grams of 4-bromo-2-ethoxycarbonyl-2,3-dihydro-2-methylbenzofuran-7-yl isocyanate. The product was taken to the next step without further characterization.

Step H

Synthesis of a mixture of
3-(4-bromo-2-ethoxycarbonyl-2,3-dihydro-
2-methylbenzofuran-7-yl
)-1-methyl-6-trifluoromethyluracil (Compound 57)
and 3-(4-bromo-2,3-dihydro-2-methoxycarbonyl-
2-methylbenzofuran-7-yl
)-1-methyl-6-trifluoromethyluracil (Compound 55)
as intermediates By the method of Example 1, Step G, 1.7 grams (0.005 mole) of 4-bromo-2-ethoxycarbonyl-2,3-dihydro-2-methylbenzofuran-7-yl isocyanate was reacted with 0.3 gram (0.006 mole) of sodium hydride and 1.0 gram (0.005 mole) of ethyl 3-amino-4,4,4-trifluorocrotonate in 45 mL of tetrahydrofuran. Subsequently, 0.9 gram (0.006 mole) of methyl iodide and 0.8 gram (0.006 mole) of potassium carbonate were reacted with the product of the first reaction, yielding a mixture of 3-(4-bromo-2-ethoxycarbonyl-2,3-dihydro-2-methylbenzofuran-7-yl )-1-methyl-6-trifluoromethyluracil and 3-(4-bromo-2,3-dihydro-2-methoxycarbonyl-2-methylbenzofuran-7-yl )-1-methyl-6-trifluoromethyluracil. The mixture was subjected to column chromatography on silica gel, with 1:4 ethyl acetate:heptane as the eluant. The appropriate product-containing fractions were combined and concentrated under reduced pressure, yielding 0.8 gram of 3-(4-bromo-2-ethoxycarbonyl-2,3-dihydro-2-methylbenzofuran-7-yl )-1-methyl-6-trifluoromethyluracil. Other appropriate product-containing fractions, as determined by thin layer chromatography, were combined and concentrated under reduced pressure, yielding 1.0 gram of 3-(4-bromo-2,3-dihydro-2-methoxycarbonyl-2-methylbenzofuran-7-yl)-1-methyl-6-trifluoromethyluracil. The NMR spectra were consistent with the proposed structures.

Step I

Synthesis of
3-(4-bromo-2,3-dihydro-2-methoxycarbonyl-
2-methylbenzofuran-3-on-7-yl)-1-
methyl-6-trifluoromethyluracil (Compound 56)

By the method of Example 3, Step A, 0.5 gram (0.001 mole) of 3-(4-bromo-2,3-dihydro-2-methoxycarbonyl-2-methylbenzofuran-7-yl )-1-methyl-6-trifluoromethyluracil (Compound 55) was reacted with 0.9 gram (0.003 mole) of potassium persulfate and 0.3 gram (0.001 mole) of copper(II) sulfate pentahydrate in 5 mL of acetonitrile and 5 mL of water. The reaction mixture was extracted with three portions of methylene chloride. The extract was dried with magnesium sulfate and filtered. The filtrate was concentrated under reduced pressure to a residue, which was subjected to column chromatography on silica gel, with 3:7 ethyl acetate:heptane as the eluant. The product-containing fractions were combined and concentrated under reduced pressure, yielding 0. 1 gram of 3-(4-bromo-2,3-dihydro-2-methoxycarbonyl-2-methylbenzofuran-3-on 7yl)-1-methyl-6-trifluoromethyluracil. The NMR spectrum was consistent with the proposed structure.

HERBICIDAL ACTIVITY

The 3-(benzofuran-7-yl)-6-haloalkyluracil herbicides of this invention were tested for pre- and postemergence herbicidal activity using a variety of crops and weeds. The test plants included soybean (*Glycine max* var. Williams), field corn (*Zea mays var.* Agway 425X), wheat (*Triticum aestivum* var. Wheaton), morningglory (*Ipomoea lacunosa* or *Ipomoea hederacea*), velvetleaf (*Abutilon theophrasti*), green foxtail (*Setaria viridis*), Johnsongrass (*Sorghum halepense*), blackgrass (*Aloepecurus myosuroides*), common chickweed (*Stellaria media*), and common cocklebur (*Xanthium pensylvanicum*).

For preemergence testing, two disposable fiber flats (8 cm×15 cm× 25 cm) for each rate of application of each candidate herbicide were filled to an approximate depth of 6.5 cm with steam-sterilized sandy loam soil. The soil was leveled and impressed with a template to provide five evenly spaced furrows 13 cm long and 0.5 cm deep in each flat. Seeds of soybean, wheat, corn, green foxtail, and Johnsongrass were planted in the furrows of the first flat, and seeds of velvetleaf, morningglory, common chickweed, cocklebur, and blackgrass were planted in the furrows of the second flat. The five-row template was employed to firmly press the seeds into place. A topping soil of equal portions of sand and sandy loam soil was placed uniformly on top of each flat to a depth of approximately 0.5 cm. Flats for postemergence testing were prepared in the same manner except that they were planted 8–12 days prior to the preemergence flats and were placed in a greenhouse and watered, thus allowing the seeds to germinate and the foliage to develop.

In both pre- and postemergence tests, a stock solution of the candidate herbicide was prepared by dissolving 0.27g of the compound in 20 mL of water/acetone (50/50) containing 0.5% v/v sorbitan monolaurate. For an application rate of 3000 g/ha of herbicide a 10 mL portion of the stock solution was diluted with water/acetone (50/50) to 45 mL. The volumes of stock solution and diluent used to prepare solutions for lower application rates are shown in the following table:

| Application Rate (g/ha) | Volume of Stock Solution (mL) | Volume of Acetone/Water (mL) | Total Volume of Spray Solution (mL) |
|---|---|---|---|
| 3000 | 10 | 35 | 45 |
| 900 | 3 | 42 | 45 |
| 300 | 1 | 44 | 45 |
| 90 | 0.3 | 35 | 45.3 |
| 30 | 0.1 | 45 | 45.1 |
| 9 | 0.03 | 45 | 45.03 |
| 3 | 0.01 | 45 | 45.01 |

The preemergence flats were initially subjected to a light water spray. The four flats were placed two by two along a conveyor belt (i.e., the two preemergence followed by the two postemergence flats). The conveyor belt fed under a spray nozzle mounted about ten inches above the postemergent foliage. The preemergent flats were elevated on the belt so that the soil surface was at the same level below the spray nozzle as the foliage canopy of the postemergent plants. The spray of herbicidal solution was commenced and once stabilized, the flats were passed under the spray at a speed to receive a coverage equivalent of 1000 L/ha. At this coverage the application rates are those shown in the above table for the individual herbicidal solutions. The preemergence flats were watered immediately thereafter, placed in the greenhouse and watered regularly at the soil surface. The postemergence flats were immediately placed in the greenhouse and not watered until 24 hours after treatment with the test solution. Thereafter they were regularly watered at ground level. After 17–21 days the plants were examined and the phytotoxicity data were recorded.

Herbicidal activity data at selected application rates are given for various compounds of this invention in Table 3 and Table 4. The test compounds are identified by numbers which correspond to those in Table 1.

Phytotoxicity data were taken as percent control. Percent control was determined by a method similar to the 0 to 100 rating system disclosed in "Research Methods in Weed Science," 2nd ed., B. Truelove, Ed.; Southern Weed Science Society; Auburn University, Auburn, Ala., 1977. The rating system is as follows:

| | Herbicide Rating System | | |
|---|---|---|---|
| Rating Percent Control | Description of Main Categories | Crop Description | Weed Description |
| 0 | No effect | No crop reduction or injury | No weed control |
| 10 | | Slight discoloration or stunting | Very poor weed control |
| 20 | Slight effect | Some discoloration, stunting or stand loss | Poor weed control |
| 30 | | Crop injury more pronounced but not lasting | Poor to deficient weed control |
| 40 | | Moderate injury, crop usually recovers | Deficient weed control |
| 50 | Moderate effect | Crop injury more lasting, recovery doubtful | Deficient to moderate weed control |
| 60 | | Lasting crop injury, no recovery | Moderate weed control |
| 70 | | Heavy injury and stand loss | Control somewhat less than satisfactory |
| 80 | Severe | Crop nearly destroyed, a few survivors | Satisfactory to good weed control |
| 90 | | Only occasional live plants left | Very good to excellent control |
| 100 | Complete effect | Complete crop destruction | Complete weed destruction |

For herbicidal application, the 3-(benzofuran-7-yl)-6-haloalkyluracils are formulated into herbicidal compositions by admixture in herbicidally effective amounts with adjuvants and carriers normally employed in the art for facilitating the dispersion of active ingredients for the particular utility desired, recognizing the fact that the formulation and mode of application of a toxicant may affect the activity of the material in a given application. Thus, for agricultural use the present herbicidal compounds may be formulated as granules of relatively large particle size, as water-soluble or water-dispersible granules, as powdery dusts, as wettable powders, as emulsifiable concentrates, as solutions, or as any of several other known types of formulations, depending on the desired mode of application.

These herbicidal compositions may be applied either as water-diluted sprays, or dusts, or granules to the areas in which suppression of vegetation is desired. These formulations may contain as little as 0.1%, 0.2% or 0.5% to as much as 95% or more by weight of active ingredient.

Dusts are free flowing admixtures of the active ingredient with finely divided solids such as talc, natural clays, kieselguhr, flours such as walnut shell and cottonseed flours, and other organic and inorganic solids which act as dispersants and carriers for the toxicant; these finely divided solids have an average particle size of less than about 50 microns. A typical dust formulation useful herein is one containing 1.0 part or less of the herbicidal compound and 99.0 parts of talc.

Wettable powders, also useful formulations for both pre- and post-emergence herbicides, are in the form of finely divided particles which disperse readily in water or other dispersants. The wettable powder is ultimately applied to the soil either as a dry dust or as an emulsion in water or other liquid. Typical carriers for wettable powders include Fuller's earth, kaolin clays, silicas, and other highly absorbent, readily wettable inorganic diluents. Wettable powders normally are prepared to contain about 5–80% of active ingredient, depending on the absorbency of the carrier, and usually also contain a small amount of a wetting, dispersing or emulsifying agent to facilitate dispersion. For example, a useful wettable powder formulation contains 80.8 parts of the herbicidal compound, 17.9 parts of Palmetto clay, 1.0 part of sodium lignosulfonate, and 0.3 part of sulfonated aliphatic polyester as wetting agents. Frequently, additional wetting agent and/or oil will be added to the tank mix for postemergence application to facilitate dispersion on the foliage and absorption by the plant.

Other useful formulations for herbicidal applications are emulsifiable concentrates (ECs) which are homogeneous liquid compositions dispersible in water or other dispersant, and may consist entirely of the herbicidal compound and a liquid or solid emulsifying agent, or may also contain a liquid carrier, such as xylene, heavy aromatic naphthas, isophorone, or other non-volatile organic solvent. For herbicidal application these concentrates are dispersed in water or other liquid carrier, and normally applied as a spray to the area to be treated. The percentage by weight of the essential active ingredient may vary according to the manner in which the composition is to be applied, but in general comprises 0.5 to 95% of active ingredient by weight of the herbicidal composition.

Flowable formulations are similar to ECs except that the active ingredient is suspended in a liquid carrier, generally water. Flowables, like ECs, may include a small amount of a surfactant, and contain active ingredient in the range of 0.5 to 95%, frequently from 10 to 50%, by weight of the composition. For application, flowables may be diluted in water or other liquid vehicle, and are normally applied as a spray to the area to be treated.

Typical wetting, dispersing or emulsifying agents used in agricultural formulations include, but are not limited to, the alkyl and alkylaryl sulfonates and sulfates and their sodium salts; alkylaryl polyether alcohols; sulfated higher alcohols; polyethylene oxides; sulfonated animal and vegetable oils; sulfonated petroleum oils; fatty acid esters of polyhydric alcohols and the ethylene oxide addition products of such esters; and the addition product of long-chain mercaptans and ethylene oxide. Many other types of useful surface-active agents are available in commerce. The surface-active agent, when used, normally comprises from 1 to 15% by weight of the composition.

Other useful formulations include suspensions of the active ingredient in a relatively non-volatile solvent such as water, corn oil, kerosene, propylene glycol, or other suitable solvents.

Still other useful formulations for herbicidal applications include simple solutions of the active ingredient in a solvent in which it is completely soluble at the desired concentration, such as acetone, alkylated naphthalenes, xylene, or other organic solvents. Granular formulations, wherein the toxicant is carried on relatively coarse particles, are of particular utility for aerial distribution or for penetration of cover crop canopy. Pressurized sprays, typically aerosols wherein the active ingredient is dispersed in finely divided form by a propellant, such as carbon dioxide, propane or butane, may also be used. Water-soluble or water-dispersible granules are also useful formulations for herbicidal application of the present compounds. Such granular formulations are free-flowing, non-dusty, and readily water-soluble or water-miscible. The soluble or dispersible granular formulations described in U.S. Pat. No. 3,920,442 are useful herein with the present herbicidal compounds. In use by the farmer on the field, the granular formulations, emulsifiable concentrates, flowable concentrates, solutions, etc., may be diluted with water to give a concentration of active ingredient in the range of say 0.1% or 0.2% to 1.5% or 2%.

The 3-(benzofuran-7-yl)-6-haloalkyluracils of this invention may be formulated and/or applied with insecticides, fungicides, nematicides, plant growth regulators, fertilizers, or other agricultural chemicals and may be used as effective soil sterilants as well as selective herbicides in agriculture. In applying an active compound of this invention, whether formulated alone or with other agricultural chemicals, an effective amount and concentration of the active compound is of course employed; the amount may be as low as, for example, about 4 to 300 g/ha to, preferably about 10 to 30 g/ha. For field use, where there are losses of herbicide, higher application rates (for example, four times the rates mentioned above) may be employed.

The 3-(benzofuran-7-yl)-6-haloalkyluracils of this invention may be used in combination with other herbicides, for example they may be mixed with, say, an equal or larger amount of a known herbicide such as aryloxyalkanoic acid herbicides such as (2,4-dichlorophenoxy)acetic acid (2,4-D), (4-chloro-2-methylphenoxy)acetic acid (MCPA), (±)-2-(4-chloro-2-methylphenoxy)propanoic acid (MCPP); urea herbicides, such as N,N-dimethyl-N-'-[4-(1-methylethyl)phenyl]urea (isoproturon); imidazolinone herbicides, such as 2-[4,5-dihydro-4-methyl-4-(1-methylethyl)-5-oxo-1H-imidazol-2-yl]-3-pyridinecarboxylic acid (imazapyr), a reaction product comprising (±)-2-[4,5-dihydro-4-methyl-4-(1-methylethyl)-5-oxo-1H-imidazol-2-yl]-4-methylbenzoic acid and (±)-2-[4,5-dihydro-4-methyl-4-(1-methylethyl)-5-oxo-1H-imidazol-2-yl]-5-methylbenzoic acid (imazamethabenz), (±)-2-[4,5-dihydro-4-methyl-4-(1-methylethyl)-5-oxo-1H-imidazol-2-yl]-5-ethyl-3-pyridinecarboxylic acid (imazethapyr),and (±)-2-[4,5-dihydro-4-methyl-4-(1-methylethyl)-5-oxo-1H-imidazol-2-yl]-3-quinolinecarboxylic acid (imazaquin); diphenyl ether herbicides, such as 5-[2-chloro-4-(trifluoromethyl)phenoxy]-2-nitrobenzoic acid (acifluorfen), methyl 5-(2,4-dichlorophenoxy)-2-nitrobenzoate (bifenox), and 5-[2-chloro-4-(trifluoromethyl)phenoxy]-N-(methylsulfonyl)-2-nitrobenzamide (fomasafen); hydroxybenzonitrile herbicides, such as 4-hydroxy-3,5-diiodobenzonitrile (ioxynil), and 3,5-dibromo-4-hydroxybenzonitrile (bromoxynil); sulfonylurea herbicides, such as 2-[[[[(4-chloro-6-methoxy-2-pyrimidinyl)amino]carbonyl]amino]sulfonyl]-benzoic acid (chlorimuron), 2-chloro-N-[[(4-methoxy-6-methyl-1,3,5-triazin-2yl)amino]carbonyl]benzenesulfonamide (chlorsulfuron), 2-[[[[[(4,6-dimethoxy-2-pyrimidinyl)amino]carbonyl]amino]sulfonyl]methyl]benzoic acid 5 (bensulfuron), 2-[[[[(4,6-dimethoxy-2-pyrimidinyl)amino]carbonyl] amino]sulfonyl]-1-methyl-1H-pyrazol-4-carboxylic acid (pyrazosulfuron), 3-[[[[(4-methoxy-6-methyl-1,3,5-triazin-2-yl)amino]carbonyl]amino]sulfonyl]-2-thiophenecarboxylic acid (thifensulfuron), and 2-(2-chloroethoxy)-N-[[(4-methoxy-6-methyl-1,3,5-triazin-2-yl)amino]carbonyl] benzenesulfonamide (triasulfron); 2-(4-aryloxyphenoxy)alkanoic acid herbicides, such as (±)-2-[4-[(6-chloro-2-benzoxazolyl)oxy]phenoxy]propanoic acid (fenoxaprop), (±)-2-[4-[[5-(trifluoromethyl)-2-pyridinyl] oxy]phenoxy]propanoic acid (fluazifop), (±)-2-[4-(6-chloro- 2-quinoxalinyl)oxy]phenoxy]propanoic acid (quizalofop), and (±)-2-[-(2,4-dichlorophenoxy)phenoxy]propanoic acid (diclofop); benzothiadiazinone herbicides, such as 3-(1-methylethyl)-1H-2,1,3-benzothiadiazin-4(3H)-one 2,2-dioxide (bentazone); 2-chloroacetanilide herbicides, such as N-(butoxymethyl)-2-chloro-2',6'-diethylacetanilide (butachlor); arenecarboxylic acid herbicides, such as 3,6-dichloro-2-methoxybenzoic acid (dicamba); and pyridyloxyacetic acid herbicides, such as [(4-amino-3,5-dichloro-6-fluoro-2-pyridinyl)oxy]acetic acid (fluroxypyr).

It is apparent that various modifications may be made in the formulation and application of the compounds of this invention without departing from the inventive concepts herein as defined in the claims.

TABLE 1

3-(Benzofuran-7-yl)-6-haloalkyluracils

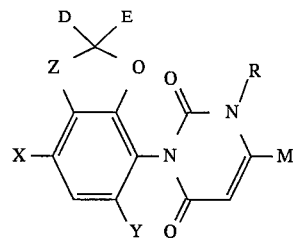

| Cmpd No. | R | D | E | M | X | Y | Z |
|---|---|---|---|---|---|---|---|
| 1 | $CH_3$ | $CH_3$ | $CH_3$ | $CF_3$ | H | H | $CH_2$ |
| 2 | $CH_3$ | $CH_3$ | $CH_3$ | $CF_3$ | F | H | $CH_2$ |
| 3 | $CH_3$ | $CH_3$ | $CH_3$ | $CF_3$ | Cl | H | $CH_2$ |
| 4 | $CH_3$ | $CH_3$ | $CH_3$ | $CF_3$ | Cl | F | $CH_2$ |
| 5 | $CH_3$ | $CH_3$ | $CH_3$ | $CF_3$ | $CH_3O$ | H | $CH_2$ |
| 6 | $CH_3$ | $CH_3$ | $CH_3$ | $CF_3$ | H | H | C=O |
| 7 | $CH_3$ | $CH_3$ | $CH_3$ | $CF_3$ | F | H | C=O |
| 8 | $CH_3$ | $CH_3$ | $CH_3$ | $CF_3$ | Cl | H | C=O |
| 9 | $C_2H_5$ | $CH_3$ | $CH_3$ | $CF_3$ | Cl | H | C=O |
| 10 | $C_3H_7$ | $CH_3$ | $CH_3$ | $CF_3$ | Cl | H | C=O |
| 11 | $i$-$C_3H_7$ | $CH_3$ | $CH_3$ | $CF_3$ | Cl | H | C=O |
| 12 | $CH_2CH=CH_2$ | $CH_3$ | $CH_3$ | $CF_3$ | Cl | H | C=O |
| 13 | $CH_2C\equiv CH$ | $CH_3$ | $CH_3$ | $CF_3$ | Cl | H | C=O |
| 14 | $(CH_2)_2CH_2F$ | $CH_3$ | $CH_3$ | $CF_3$ | Cl | H | C=O |
| 15 | $CH_2OCH_3$ | $CH_3$ | $CH_3$ | $CF_3$ | Cl | H | C=O |
| 16 | $CH_2CN$ | $CH_3$ | $CH_3$ | $CF_3$ | Cl | H | C=O |
| 17 | $CH_2CO_2C_2H_5$ | $CH_3$ | $CH_3$ | $CF_3$ | Cl | H | C=O |
| 18 | $-CH_2$-phenyl | $CH_3$ | $CH_3$ | $CF_3$ | Cl | H | C=O |
| 19 | $CH_3$ | $CH_3$ | $CH_3$ | $CF_3$ | H | Cl | C=O |
| 20 | $CH_3$ | $CH_3$ | $CH_3$ | $CF_3$ | Br | H | C=O |
| 21 | $CH_3$ | $CH_3$ | $CH_3$ | $CF_3$ | Cl | F | C=O |
| 22 | $CH_3$ | $CH_3$ | $CH_3$ | $CF_3$ | Cl | Cl | C=O |
| 23 | $CH_3$ | $CH_3$ | $CH_3$ | $CF_3$ | Br | Br | C=O |
| 24 | $CH_3$ | $CH_3$ | $CH_3$ | $CF_3$ | $CH_3O-$ | H | C=O |
| 25 | $CH_3$ | $CH_3$ | $CH_3$ | $CF_3$ | $C_2H_5O-$ | Cl | C=O |
| 26 | $CH_3$ | $CH_3$ | $CH_3$ | $CF_3$ | Cl | Cl | $C=NOCH_3$ |
| 27 | $CH_3$ | $CH_3$ | $CH_3$ | $CF_3$ | Br | H | $C=NOCH_3$ |
| 28 | $CH_3$ | $CH_3$ | H | $CF_3$ | Cl | H | C=O |
| 29 | $CH_3$ | $CH_3$ | $C_2H_5$ | $CF_3$ | Cl | H | C=O |
| 30 | $CH_3$ | H | H | $CF_3$ | Cl | H | C=O |
| 31 | $CH_3$ | $-CH_2CH_2-$ | | $CF_3$ | Cl | H | C=O |
| 32 | $CH_3$ | $C_2H_5$ | $C_2H_5$ | $CF_3$ | Cl | H | C=O |
| 33 | $CH_3$ | $CH_3$ | $CH_3$ | $CF_3$ | $-CN$ | H | C=O |
| 34 | $CH_3$ | $CH_3$ | $CH_3$ | $CF_3$ | $CH_3$ | H | C=O |
| 35 | $CH_3$ | $CH_3$ | $CH_3$ | $CF_3$ | $CF_3$ | H | C=O |
| 36 | $CH_3$ | $CH_3$ | $CH_3$ | $CF_3$ | $CF_3O$ | H | C=O |
| 37 | $CH_3$ | $CH_3$ | $CH_3$ | $CF_2CF_3$ | Cl | H | C=O |
| 38 | $CH_3$ | $CH_3$ | $CH_3$ | $CF_3$ | Cl | H | C=S |
| 39 | $CH_3$ | $CH_3$ | $CH_3$ | $CF_3$ | Cl | F | CH(OH) |
| 40 | $CH_3$ | H | H | $CF_3$ | Cl | F | $CH_2CH_2$ |
| 41 | $CH_3$ | $CH_3$ | $CH_3$ | $CF_3$ | Cl | F | $CH_2CH_2$ |
| 42 | $CH_3$ | $CH_3$ | $CH_3$ | $CF_3$ | Cl | H | $CH_2CH_2$ |

TABLE 1-continued 3-(Benzofuran-7-yl)-6-haloalkyluracils

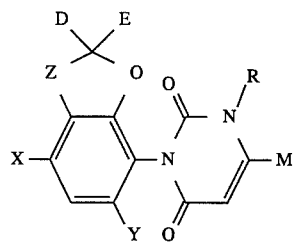

| Cmpd No. | R | D | E | M | X | Y | Z |
|---|---|---|---|---|---|---|---|
| 43 | NH$_2$ | CH$_3$ | CH$_3$ | CF$_3$ | Cl | H | CH$_2$CH$_2$ |
| 44 | CH$_3$ | CH$_3$ | CH$_3$ | CF$_3$ | Cl | Cl | CH$_2$CH$_2$ |
| 45 | NH$_2$ | CH$_3$ | CH$_3$ | CF$_3$ | Cl | Cl | CH$_2$CH$_2$ |
| 46 | CH$_3$ | H | H | CF$_3$ | Cl | F | (C=O)CH$_2$ |
| 47 | CH$_3$ | CH$_3$ | CH$_3$ | CF$_3$ | Cl | F | (C=O)CH$_2$ |
| 48 | CH$_3$ | CH$_3$ | CH$_3$ | CF$_3$ | Cl | Cl | (C=O)CH$_2$ |
| 49 | —CH$_3$ | CH$_3$ | CH$_3$ | CF$_3$ | Cl | H | (C=O)CH$_2$ |
| 50 | CH$_3$ | CH$_3$ | CH$_3$ | CF$_3$ | Cl | F | CH=CH |
| 51 | CH$_3$ | CH$_3$ | CH$_3$ | CF$_3$ | Cl | Cl | CH=CH |
| 52 | NH$_2$ | CH$_3$ | CH$_3$ | CF$_3$ | Cl | Cl | CH=CH |
| 53 | NH$_2$ | CH$_3$ | CH$_3$ | CF$_3$ | Cl | H | CH=CH |
| 54 | CH$_3$ | CH$_3$ | CH$_3$ | CF$_3$ | Cl | H | CH=CH |
| 55 | CH$_3$ | CO$_2$CH$_3$ | CH$_3$ | CF$_3$ | Br | H | CH$_2$ |
| 56 | CH$_3$ | CO$_2$CH$_3$ | —CH$_3$ | CF$_3$ | Br | H | C=O |
| 57 | CH$_3$ | CO$_2$C$_2$H$_5$ | CH$_3$ | CF$_3$ | Br | H | CH$_2$ |
| 58 | NH$_2$ | CH$_3$ | CH$_3$ | CF$_3$ | Cl | H | CH$_2$ |
| 59 | NH$_2$ | CH$_3$ | CH$_3$ | CF$_3$ | Cl | Cl | C=O |
| 60 | NH$_2$ | CH$_3$ | CH$_3$ | CF$_3$ | Cl | H | C=O |
| 61 | CH$_3$ | CH$_3$ | CH$_3$ | CF$_3$ | CH$_3$ | H | C=O |
| 62 | CH$_3$ | CH$_3$ | CH$_3$ | CF$_3$ | CH$_3$ | H | CH$_2$ |
| 63 | NH$_2$ | CH$_3$ | CH$_3$ | CF$_3$ | Cl | CH$_3$ | CH$_2$ |
| 64 | CH$_3$ | CH$_3$ | CH$_3$ | CF$_3$ | Cl | CH$_3$ | CH$_2$— |
| 65 | CH$_3$ | CH$_3$ | CH$_3$ | CF$_3$ | Cl | CH$_3$ | C=O |

TABLE 1A

3-Benzofuran-7-yl-6-trifluoromethyluracils

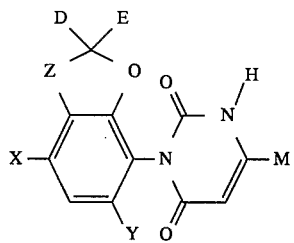

wherein D and E are CH$_3$ and M is CF$_3$

| Compound No. | X | Y | Z |
|---|---|---|---|
| 1A | H | H | CH$_2$ |
| 2A | Cl | F | CH$_2$ |
| 3A | CH$_3$ | H | CH$_2$ |
| 4A | H | H | C=O |
| 5A | F | H | C=O |
| 6A | Cl | H | C=O |
| 7A | H | Cl | C=O |
| 8A | Br | H | C=O |
| 9A | Cl | Cl | C=O |
| 10A | Br | Br | C=O |
| 11A | CH$_3$ | H | C=O |

TABLE 2

Characterizing Properties

| Cmpd. No. | mp (°C.) | Cmpd No. | mp (°C.) |
|---|---|---|---|
| 1 | 119.5–121.5 | 39 | 82–83 |
| 2 | 157–158 | 40 | 141–145 |
| 3 | 152–153 | 41 | 132–135 |
| 4 | 125–127 | 42 | 123–124 |
| 5 | 201–203 | 43 | oil |
| 6 | 136–137 | 44 | 139–140 |
| 7 | 178–180 | 45 | oil |
| 8 | 177–178 | 46 | 203–205 |
| 9 | oil | 47 | oil |
| 10 | oil | 48 | oil |
| 11 | 179–180 | 49 | oil |
| 12 | oil | 50 | oil |
| 13 | 76–78 | 51 | 134–138 |
| 14 | oil | 52 | 91 dec |
| 15 | oil | 53 | oil |
| 16 | 91–92 | 54 | oil |
| 17 | oil | 55 | 50–55 |
| 18 | oil | 56 | 80–85 |
| 19 | 182.5–184 | 57 | oil |
| 20 | 170–172 | 58 | liquid |
| 21 | 160–162 | 59 | 210–214 |
| 22 | 186–187 | 60 | 70–72 |
| 23 | 181–183 | 61 | 179.5–182 |
| 24 | 222.5–224 | 62 | 151–152 |
| 25 | 162–164 | 63 | liquid |
| 26 | 145–149 | 64 | 178–178.5 |
| 27 | 84–87 | 65 | oil |
| 34 | 179.5–182 | | |

TABLE 3

PREEMERGENCE HERBICIDAL ACTIVITY (% CONTROL)

| Compound No. | 1 | 2 | 3 | 4 |
|---|---|---|---|---|
| Rate(kg/ha) | 0.3 | 0.3 | 0.3 | 0.3 |
| Species | | | | |
| Soybean | 60 | 100 | 100 | 100 |
| Wheat | 10 | 60 | 100 | 100 |
| Corn | 30 | 95 | 100 | 100 |
| Velvetleaf | 100 | 100 | 100 | 100 |
| Morningglory | 90 | 100 | 100 | 100 |
| Chickweed | 95 | 95 | 100 | 100 |
| Cocklebur | 60 | 90 | 100 | 100 |
| Blackgrass | 20 | 70 | 95 | 100 |
| Green foxtail | 100 | 100 | 100 | 100 |
| Johnsongrass | 30 | 100 | 100 | 100 |

| Compound No. | 5 | 6 | 7 | 8 |
|---|---|---|---|---|
| Rate(kg/ha) | 0.3 | 0.3 | 0.3 | 0.3 |
| Species | | | | |
| Soybean | 80 | 100 | 90 | 100 |
| Wheat | 0 | 95 | 90 | 100 |
| Corn | 80 | 95 | 95 | 100 |
| Velvetleaf | 100 | 100 | 100 | 100 |
| Morningglory | 70 | 100 | 100 | 100 |
| Chickweed | 80 | 100 | 100 | 100 |
| Cocklebur | 20 | 100 | 100 | 100 |
| Blackgrass | 20 | 100 | 100 | 100 |
| Green foxtail | 90 | 100 | 100 | 100 |
| Johnsongrass | 60 | 100 | 100 | 100 |

| Compound No. | 9 | 10 | 11 | 12 |
|---|---|---|---|---|
| Rate(kg/ha) | 0.3 | 0.3 | 0.3 | 0.3 |
| Species | | | | |
| Soybean | 60 | 0 | 10 | 10 |
| Wheat | 100 | 0 | 10 | 20 |
| Corn | 95 | 20 | 10 | 70 |
| Velvetleaf | 100 | 30 | 100 | 95 |
| Morningglory | 80 | 0 | 40 | 0 |
| Chickweed | 20 | 0 | 10 | 0 |
| Cocklebur | 0 | 0 | 0 | 0 |
| Blackgrass | 90 | 0 | 0 | 30 |
| Green foxtail | 100 | 0 | 75 | 50 |
| Johnsongrass | 100 | 20 | 70 | 80 |

| Compound No. | 13 | 14 | 15 | 16 |
|---|---|---|---|---|
| Rate(kg/ha) | 0.3 | 0.3 | 0.3 | 0.3 |
| Species | | | | |
| Soybean | 95 | 50 | 100 | 100 |
| Wheat | 100 | 40 | 100 | 95 |
| Corn | 90 | 85 | 95 | 100 |
| Velvetleaf | 100 | 100 | 100 | 100 |
| Morningglory | 60 | 75 | 80 | 100 |
| Chickweed | 100 | 0 | 80 | 100 |
| Cocklebur | 0 | 0 | 0 | 60 |
| Blackgrass | 100 | 40 | 80 | 100 |
| Green foxtail | 100 | 95 | 100 | 100 |
| Johnsongrass | 100 | 95 | 100 | 100 |

| Compound No. | 17 | 18 | 19 | 22 |
|---|---|---|---|---|
| Rate(kg/ha) | 0.3 | 0.3 | 0.3 | 0.3 |
| Species | | | | |
| Soybean | 40 | 20 | 30 | 100 |
| Wheat | 20 | 50 | 50 | 100 |
| Corn | 75 | 80 | 85 | 100 |
| Velvetleaf | 95 | 100 | 100 | 100 |
| Morningglory | 75 | 20 | 75 | 100 |
| Chickweed | 70 | 40 | 0 | 100 |
| Cocklebur | 0 | 0 | 0 | 100 |
| Blackgrass | 50 | 80 | 25 | 100 |
| Green foxtail | 40 | 70 | 100 | 100 |
| Johnsongrass | 80 | 95 | 100 | 100 |

| Compound No. | 21 | 22 | 23 | 24 |
|---|---|---|---|---|
| Rate(kg/ha) | 0.3 | 0.3 | 0.3 | 0.3 |
| Species | | | | |
| Soybean | 100 | 100* | 80 | 90 |
| Wheat | 95 | 100* | 90 | 20 |
| Corn | 60 | 95* | 95 | 85 |
| Velvetleaf | 100 | 100* | 100 | 100 |
| Morningglory | 100 | 75* | 95 | 100 |
| Chickweed | 100 | 35* | 100 | 90 |
| Cocklebur | 100 | 50* | 30 | 70 |
| Blackgrass | 100 | 95* | 85 | 40 |
| Green foxtail | 100 | 100* | 100 | 95 |
| Johnsongrass | 100 | 100* | 100 | 75 |

| Compound No. | 25 | 26 | 27 | 39 |
|---|---|---|---|---|
| Rate(kg/ha) | 0.3 | 0.3 | 0.3 | 0.3 |
| Species | | | | |
| Soybean | 10 | 40 | 60 | 100 |
| Wheat | 0 | 25 | 25 | 100 |
| Corn | 20 | 90 | 95 | 100 |
| Velvetleaf | 90 | 100 | 100 | 100 |
| Morningglory | 0 | 100 | 90 | 100 |
| Chickweed | 0 | 0 | 100 | 80 |
| Cocklebur | 0 | 10 | 35 | 100 |
| Blackgrass | 0 | 95 | 100 | 100 |
| Green foxtail | 10 | 100 | 100 | 100 |
| Johnsongrass | 0 | 100 | 100 | 100 |

| Compound No. | 40 | 41 | 42 | 43 |
|---|---|---|---|---|
| Rate(kg/ha) | 0.3 | 0.3 | 0.3 | 0.3 |
| Species | | | | |
| Soybean | 100 | 100 | 65 | 100 |
| Wheat | 60 | 80 | 70 | 80 |
| Corn | 95 | 80 | 85 | 95 |
| Velvetleaf | 100 | 100 | 100 | 100 |
| Morningglory | 100 | 100 | 100 | 100 |
| Chickweed | 100 | 90 | 5 | 30 |
| Cocklebur | 95 | 70 | 40 | 70 |
| Blackgrass | 100 | 80 | ND | ND |
| Green foxtail | 100 | 100 | 85 | 100 |
| Johnsongrass | 95 | 100 | 75 | 95 |

| Compound No. | 44 | 45 | 46 | 47 |
|---|---|---|---|---|
| Rate(kg/ha) | 0.3 | 0.3 | 0.3 | 0.3 |
| Species | | | | |
| Soybean | 40 | 60 | 80 | lo |
| Wheat | 40 | 60 | 60 | 100 |
| Corn | 80 | 80 | 80 | 80 |
| Velvetleaf | 100 | 100 | 100 | 100 |
| Morningglory | 40 | 100 | 90 | 100 |
| Chickweed | 0 | ND | 100 | 100 |
| Cocklebur | 0 | 20 | 85 | 100 |
| Blackgrass | ND | ND | 80 | 95 |
| Green foxtail | 100 | 95 | 100 | 100 |
| Johnsongrass | 95 | 80 | 95 | 95 |

| Compound No. | 48 | 49 | 50 | 51 |
|---|---|---|---|---|
| Rate(kg/ha) | 0.3 | 0.3 | 0.3 | 0.3 |
| Species | | | | |
| Soybean | 60 | 100 | 100 | 40 |
| Wheat | 70 | 90 | 60 | 50 |
| Corn | 90 | 100 | 90 | 70 |

TABLE 3-continued

PREEMERGENCE HERBICIDAL ACTIVITY
(% CONTROL)

| | | | | |
|---|---|---|---|---|
| Velvetleaf | 100 | 100 | 100 | 80 |
| Morningglory | 35 | 100 | 100 | 50 |
| Chickweed | 0 | 90 | 100 | 0 |
| Cocklebur | 0 | 50 | 90 | ND |
| Blackgrass | ND | ND | 90 | 20 |
| Green foxtail | 100 | 100 | 100 | 100 |
| Johnsongrass | 100 | 100 | 100 | 80 |
| Compound No. | 52 | 53 | 54 | 51 |
| Rate(kg/ha) Species | 0.3 | 0.3 | 0.3 | 0.3 |
| Soybean | 50 | 90 | 70 | 0 |
| Wheat | 40 | 70 | 60 | 80 |
| Corn | 70 | 95 | 90 | 80 |
| Velvetleaf | 100 | 100 | 100 | 100 |
| Morningglory | 100 | 100 | 100 | 100 |
| Chickweed | 5 | 80 | 30 | 50 |
| Cocklebur | 10 | 70 | 60 | 100 |
| Blackgrass | 10 | 60 | 60 | 70 |
| Green foxtail | 100 | 100 | 100 | 95 |
| Johnsongrass | 70 | 80 | 80 | 100 |
| Compound No. | 56 | 57 | 58 | 59 |
| Rate(kg/ha) Species | 0.3 | 0.3 | 0.3 | 0.3 |
| Soybean | 0 | 40 | 100 | 90 |
| Wheat | 20 | 100 | 100 | 100 |
| Corn | 100 | 100 | 100 | 100 |
| Velvetleaf | 100 | 100 | 100 | 100 |
| Morningglory | 90 | 100 | 100 | 100 |
| Chickweed | 70 | 95 | 100 | 10 |
| Cocklebur | 30 | 100 | 100 | 50 |
| Blackgrass | 70 | 100 | 95 | 100 |
| Green foxtail | 90 | 100 | 100 | 100 |
| Johnsongrass | 90 | 100 | 100 | 100 |
| Compound No. | 60 | 61 | 62 | 63 |
| Rate(kg/ha) Species | 0.3 | 0.3 | 0.3 | 0.3 |
| Soybean | 100 | 100 | 80 | 60 |
| Wheat | 100 | 100 | 40 | 60 |
| Corn | 100 | 100 | 80 | 80 |
| Velvetleaf | 100 | 100 | 95 | 100 |
| Morningglory | 100 | 100 | 100 | 100 |
| Chickweed | 100 | 90 | 30 | 0 |
| Cocklebur | 100 | 100 | 40 | 30 |
| Blackgrass | 100 | 95 | 40 | 60 |
| Green foxtail | 100 | 100 | 90 | 100 |
| Johnsongrass | 100 | 100 | 90 | 90 |
| Compound No. | 64 | 65 | | |
| Rate(kg/ha) Species | 0.3 | 0.3 | | |
| Soybean | 0 | 100 | | |
| Wheat | 0 | 100 | | |
| Corn | 0 | 100 | | |
| Velvetleaf | 0 | 100 | | |
| Morningglory | 0 | 100 | | |
| Chickweed | 0 | 70 | | |
| Cocklebur | 0 | 5 | | |
| Blackgrass | 0 | 95 | | |
| Green foxtail | 0 | 100 | | |
| Johnsongrass | 0 | 100 | | |

*Average of three results

TABLE 4

POSTEMERGENCE HERBICIDAL ACTIVITY
(% CONTROL)

| Compound No. | 1 | 2 | 3 | 4 |
|---|---|---|---|---|
| Rate(kg/ha) Species | 0.3 | 0.3 | 0.3 | 0.3 |
| Soybean | 75 | 95 | 95 | 100 |
| Wheat | 0 | 40 | 65 | 95 |
| Corn | 40 | 70 | 85 | 100 |
| Velvetleaf | 100 | 100 | 100 | 100 |
| Morningglory | 80 | 100 | 100 | 100 |
| Chickweed | 20 | ND | 100 | 100 |
| Cocklebur | 40 | 95 | 100 | 100 |
| Blackgrass | 0 | 10 | 85 | 90 |
| Green foxtail | 75 | 100 | 100 | 100 |
| Johnsongrass | 40 | 80 | 100 | 100 |
| Compound No. | 5 | 6 | 7 | 8 |
| Rate(kg/ha) Species | 0.3 | 0.3 | 0.3 | 0.3 |
| Soybean | 60 | 95 | 90 | 100 |
| Wheat | 10 | 70 | 40 | 100 |
| Corn | 30 | 80 | 90 | 100 |
| Velvetleaf | 75 | 100 | 100 | 100 |
| Morningglory | 85 | 85 | 90 | 100 |
| Chickweed | 0 | 90 | 100 | 100 |
| Cocklebur | 40 | ND | 100 | 100 |
| Blackgrass | 10 | 40 | 75 | 100 |
| Green foxtail | 30 | 90 | 100 | 100 |
| Johnsongrass | 50 | 90 | 100 | 100 |
| Compound No. | 9 | 10 | 11 | 12 |
| Rate(kg/ha) Species | 0.3 | 0.3 | 0.3 | 0.3 |
| Soybean | 70 | 55 | 40 | 70 |
| Wheat | 50 | 10 | 0 | 0 |
| Corn | 70 | 20 | 0 | 40 |
| Velvetleaf | 95 | 80 | 10 | 80 |
| Morningglory | 95 | 40 | 0 | 40 |
| Chickweed | 80 | 0 | 0 | 80 |
| Cocklebur | 20 | 0 | 0 | 0 |
| Blackgrass | 50 | 0 | 0 | 50 |
| Green foxtail | 90 | 70 | 10 | 50 |
| Johnsongrass | 70 | 10 | 0 | 0 |
| Compound No. | 13 | 14 | 15 | 16 |
| Rate(kg/ha) Species | 0.3 | 0.3 | 0.3 | 0.3 |
| Soybean | 60 | 60 | 90 | 70 |
| Wheat | 75 | 20 | 30 | 100 |
| Corn | 95 | 60 | 90 | 90 |
| Velvetleaf | 100 | 90 | 100 | 100 |
| Morningglory | 60 | 70 | 75 | 80 |
| Chickweed | 50 | 50 | 0 | 100 |
| Cocklebur | 0 | 0 | 0 | 50 |
| Blackgrass | 90 | 0 | 30 | 100 |
| Green foxtail | 100 | 70 | 80 | 100 |
| Johnsongrass | 100 | 0 | 80 | 70 |
| Compound No. | 17 | 18 | 19 | 20 |
| Rate(kg/ha) Species | 0.3 | 0.3 | 0.3 | 0.3 |
| Soybean | 20 | 90 | 65 | 95 |
| Wheat | 0 | 0 | 30 | 100 |
| Corn | 0 | 40 | 80 | 100 |
| Velvetleaf | 30 | 90 | 100 | 100 |
| Morningglory | 10 | 90 | 30 | 100 |
| Chickweed | 70 | 80 | 0 | 100 |
| Cocklebur | 0 | 10 | ND | 100 |

TABLE 4-continued

POSTEMERGENCE HERBICIDAL ACTIVITY
(% CONTROL)

| | | | | |
|---|---|---|---|---|
| Blackgrass | 60 | 0 | 10 | 100 |
| Green foxtail | 40 | 90 | 95 | 100 |
| Johnsongrass | 0 | 0 | 90 | 100 |

| Compound No. | 21 | 22 | 23 | 24 |
|---|---|---|---|---|
| Rate(kg/ha) | 0.3 | 0.3 | 0.3 | 0.3 |
| Species | | | | |
| Soybean | 95 | 70* | 75 | 90 |
| Wheat | 100 | 85* | 30 | 0 |
| Corn | 80 | 85* | 90 | 0 |
| Velvetleaf | 100 | 100* | 100 | 75 |
| Morningglory | 100 | 65* | 75 | 75 |
| Chickweed | 100 | 30* | 0 | 10 |
| Cocklebur | 100 | 20** | ND | 50 |
| Blackgrass | 100 | 80* | 10 | 30 |
| Green foxtail | 100 | 100* | 100 | 30 |
| Johnsongrass | 100 | 95* | 90 | 10 |

| Compound No. | 25 | 26 | 27 | 39 |
|---|---|---|---|---|
| Rate(kg/ha) | 0.3 | 0.3 | 0.3 | 0.3 |
| Species | | | | |
| Soybean | 20 | 80 | 90 | 100 |
| Wheat | 0 | 20 | 40 | 80 |
| Corn | 10 | 90 | 80 | 90 |
| Velvetleaf | 0 | 100 | 100 | 100 |
| Morningglory | 0 | 100 | 100 | 100 |
| Chickweed | 0 | 10 | 100 | 100 |
| Cocklebur | 0 | 95 | 100 | 100 |
| Blackgrass | 0 | 20 | 30 | 80 |
| Green foxtail | 30 | 100 | 100 | 100 |
| Johnsongrass | 0 | 100 | 100 | 100 |

| Compound No. | 40 | 41 | 42 | 43 |
|---|---|---|---|---|
| Rate(kg/ha) | 0.3 | 0.3 | 0.3 | 0.3 |
| Species | | | | |
| Soybean | 95 | 95 | 95 | 95 |
| Wheat | 60 | 50 | 60 | 60 |
| Corn | 80 | 75 | 75 | 80 |
| Velvetleaf | 100 | 100 | 100 | 100 |
| Morningglory | 100 | 100 | 100 | 100 |
| Chickweed | 100 | 80 | 70 | 60 |
| Cocklebur | 100 | 100 | 60 | 90 |
| Blackgrass | 100 | 50 | 50 | 50 |
| Green foxtail | 100 | 100 | 95 | 100 |
| Johnsongrass | 100 | 100 | 70 | 80 |

| Compound No. | 44 | 45 | 46 | 47 |
|---|---|---|---|---|
| Rate(kg/ha) | 0.3 | 0.3 | 0.3 | 0.3 |
| Species | | | | |
| Soybean | 95 | 90 | 85 | 95 |
| Wheat | 45 | 50 | 50 | 70 |
| Corn | 70 | 70 | 60 | 70 |
| Velvetleaf | 100 | 100 | 100 | 100 |
| Morningglory | 90 | 100 | 100 | 100 |
| Chickweed | 0 | 0 | 100 | 100 |
| Cocklebur | 30 | 20 | 50 | 100 |
| Blackgrass | 20 | 30 | 20 | 90 |
| Green foxtail | 80 | 100 | 75 | 90 |
| Johnsongrass | 80 | 75 | 70 | 90 |

| Compound No. | 48 | 49 | 50 | 51 |
|---|---|---|---|---|
| Rate(kg/ha) | 0.3 | 0.3 | 0.3 | 0.3 |
| Species | | | | |
| Soybean | 70 | 95 | 95 | 80 |
| Wheat | 50 | 60 | 50 | 30 |
| Corn | 70 | 70 | 80 | 55 |
| Velvetleaf | 100 | 100 | 100 | 100 |
| Morningglory | 50 | 100 | 100 | 100 |
| Chickweed | 0 | 50 | 95 | 0 |
| Cocklebur | 30 | 95 | 100 | 50 |
| Blackgrass | 50 | 50 | 60 | 0 |
| Green foxtail | 70 | 75 | 100 | 75 |
| Johnsongrass | 70 | 70 | 95 | 60 |

| Compound No. | 52 | 53 | 54 | 51 |
|---|---|---|---|---|
| Rate(kg/ha) | 0.3 | 0.3 | 0.3 | 0.3 |
| Species | | | | |
| Soybean | 70 | 90 | 80 | 80 |
| Wheat | 45 | 60 | 60 | 100 |
| Corn | 65 | 80 | 80 | 70 |
| Velvetleaf | 100 | 100 | 100 | 100 |
| Morningglory | 100 | 100 | 100 | 100 |
| Chickweed | 0 | 15 | 0 | 100 |
| Cocklebur | 30 | 100 | 100 | 100 |
| Blackgrass | 0 | 50 | 30 | ND |
| Green foxtail | 90 | 95 | 95 | 100 |
| Johnsongrass | 70 | 90 | 75 | 100 |

| Compound No. | 56 | 57 | 58 | 59 |
|---|---|---|---|---|
| Rate(kg/ha) | 0.3 | 0.3 | 0.3 | 0.3 |
| Species | | | | |
| Soybean | 55 | 70 | 100 | 70 |
| Wheat | 10 | 100 | 70 | 80 |
| Corn | 60 | 60 | 90 | 90 |
| Velvetleaf | 100 | 100 | 100 | 100 |
| Morningglory | 10 | 100 | 100 | 100 |
| Chickweed | 70 | 80 | 100 | 0 |
| Cocklebur | 15 | 100 | 100 | 30 |
| Blackgrass | ND | ND | 100 | 100 |
| Green foxtail | 90 | 100 | 100 | 100 |
| Johnsongrass | 70 | 100 | 100 | 100 |

| Compound No. | 60 | 61 | 62 | 63 |
|---|---|---|---|---|
| Rate(kg/ha) | 0.3 | 0.3 | 0.3 | 0.3 |
| Species | | | | |
| Soybean | 100 | 100 | 80 | 70 |
| Wheat | 100 | 70 | 10 | 50 |
| Corn | 100 | 90 | 60 | 65 |
| Velvetleaf | 100 | 100 | 100 | 100 |
| Morningglory | 100 | 100 | 95 | 90 |
| Chickweed | 100 | 90 | 5 | 0 |
| Cocklebur | 100 | 100 | 30 | 10 |
| Blackgrass | 100 | 90 | 10 | 20 |
| Green foxtail | 100 | 100 | 65 | 75 |
| Johnsongrass | 100 | 100 | 40 | 70 |

| Compound No. | 64 | 65 |
|---|---|---|
| Rate(kg/ha) | 0.3 | 0.3 |
| Species | | |
| Soybean | 0 | 70 |
| Wheat | 0 | 70 |
| Corn | 0 | 80 |
| Velvetleaf | 0 | 100 |
| Morningglory | 0 | 100 |
| Chickweed | 0 | 0 |
| Cocklebur | 0 | 5 |
| Blackgrass | 0 | ND |
| Green foxtail | 0 | 100 |
| Johnsongrass | 0 | 80 |

ND = no data
*Average of three results
**Average of two results

I claim:
1. A compound of the formula:

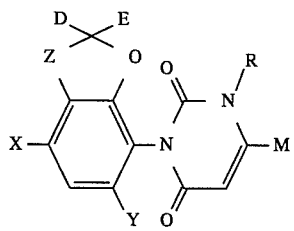

in which

M is fluoroalkyl($C_{1-6}$); D is hydrogen, alkyl($C_{1-6}$), or alkoxy($C_{1-6}$)-carbonyl; E is hydrogen or alkyl($C_{1-6}$), or D and E taken together are —$CH_2CH_2$—; R is hydrogen, alkyl($C_{1-6}$), 2-alkenyl($C_{3-6}$), 2-alkynyl($C_{3-6}$), alkoxy($C_{1-6}$)methyl, cyanoalkyl($C_{1-6}$), benzyl, fluoroalkyl($C_{1-6}$), amino, or alkoxy($C_{1-6}$)carbonylmethyl; X is hydrogen, fluorine, chlorine, bromine, cyano, alkyl($C_{1-6}$), haloalkyl($C_{1-6}$), haloalkoxy($C_{1-6}$), or alkoxy($C_{1-6}$); Y is hydrogen, fluorine, chlorine, or bromine; and Z is $CH_2$, C=O, —CH(OH)—, —$CH_2CH_2$—, —CH=CH—, —(C=O)$CH_2$—, C=S, or C=N—O—R' wherein R' is alkyl($C_{1-6}$).

2. A compound of claim 1 in which M is fluoroalkyl($C_{1-3}$); D is hydrogen, alkyl($C_{1-3}$), or alkoxy($C_{1-3}$)carbonyl; E is hydrogen or alkyl($C_{1-3}$), or D and E taken together are —$CH_2CH_2$—; R is hydrogen, alkyl($C_{1-3}$), 2alkenyl($C_{1-3}$), 2-alkenyl($C_{3-4}$), 2-alkynyl($C_{3-4}$), alkoxy($C_{1-3}$)methyl, cyanoalkyl($C_{1-3}$), benzyl, fluoroalkyl($C_{1-3}$), amino, or alkoxy($C_{1-3}$)carbonylmethyl; X is hydrogen, fluorine, chlorine, bromine, cyano, alkyl($C_{1-3}$), haloalkyl($C_{1-3}$), haloalkoxy($C_{1-3}$),or alkoxy($C_{1-3}$); Y is hydrogen, fluorine, chlorine, or bromine; and Z is $CH_2$, C=O, —CH(OH)—, —$CH_2CH_2$—, —CH=CH—, —(C=O)$CH_2$—, C=S, or C=N—O—R' wherein R' is alkyl($C_{1-3}$).

3. A compound of claim 1 in which M is fluoromethyl, or fluoroethyl; R is hydrogen, methyl, ethyl, or amino; E is hydrogen, methyl, or ethyl; D is methyl, ethyl, or methoxycarbonyl; Z is $CH_2$, C=O, —CH(OH)—, —$CH_2CH_2$—, —CH=CH—, —(C=O)$CH_2$—, or C=NOCH$_3$; and X and Y are independently hydrogen, fluorine, chlorine, or bromine.

4. A compound of claim 3 in which M is trifluoromethyl or pentafluoroethyl; R is hydrogen or methyl; E is methyl or ethyl; D is methyl or ethyl; Z is C=O; X is fluorine or chlorine; and Y is hydrogen, fluorine, chlorine, or bromine.

5. A compound of claim 4 in which M is trifluoromethyl, R is methyl; E is methyl; D is methyl; Z is C=O; and Y is hydrogen and X is fluorine or chlorine; or X is fluorine or chlorine and Y is fluorine, chlorine or bromine.

6. The compound of claim 1 which is 3-(4-chloro-2,3-dihydro-2,2-dimethylbenzofuran-3-on-7-yl)-1-methyl-6-trifluoromethyluracil.

7. The compound of claim 1 which is 3-(4-fluoro-2,3-dihydro-2,2-dimethylbenzofuran-3-on-7-yl)-1-methyl-6-trifluoromethyluracil.

8. The compound of claim 1 which is 3-(4-bromo-2,3-dihydro-2,2-dimethylbenzofuran-3-on-7-yl)-1-methyl-6-trifluoromethyluracil.

9. The compound of claim 1 which is 3-(4-chloro-6-fluoro-2,3-dihydro-2,2-dimethylbenzofuran-3-on-7-yl)-1-methyl-6-trifluoromethyluracil.

10. The compound of claim 1 which is 3-(4,6-dichloro-2,3-dihydro-2,2-dimethylbenzofuran-3-on-7-yl)-1-methyl-6-trifluoromethyluracil.

11. The compound of claim 1 which is 3-(4-chloro-6-bromo-2,3-dihydro-2,2-dimethylbenzofuran-3-on-7-yl)-1-methyl-6-trifluoromethyluracil.

12. The compound of claim 1 which is 3-(4-fluoro-6-chloro-2,3-dihydro-2,2-dimethylbenzofuran-3-on-7-yl)-1-methyl-6-trifluoromethyluracil.

13. The compound of claim 1 which is 3-(4,6-difluoro-2,3-dihydro-2,2-dimethylbenzofuran-3-on-7-yl)-1-methyl-6-trifluoromethyluracil.

14. A compound of claim 3 in which M is trifluoromethyl or pentafluoroethyl; R is methyl or amino; E is methyl or ethyl; D is methyl, ethyl, or methoxycarbonyl; Z is $CH_2$, C=O, —CH(OH)—, —$CH_2CH_2$—, —CH=CH—, —(C=O)$CH_2$—, or C=NOCH$_3$; X is bromine, fluorine, or chlorine; and Y is hydrogen, fluorine, chlorine, or bromine.

15. A compound of claim 14 in which M is trifluoromethyl; R is methyl or amino; E is methyl; D is methyl or methoxycarbonyl; Z is $CH_2$, C=O, —CH(OH)—, —$CH_2CH_2$—, —CH=CH—, —(C=O)$CH_2$—, or C=NOCH$_3$; X is bromine or chlorine; and Y is hydrogen or fluorine.

16. A compound of claim 15 in which M is trifluoromethyl; R is methyl or amino; E is methyl; D is methyl; Z is $CH_2$, C=O, —CH(OH)—, —$CH_2CH_2$—, —CH=CH—, —(C=O)$CH_2$—, or C=NOCH$_3$; X is chlorine; and Y is hydrogen or fluorine.

17. The compound of claim 16 in which M is trifluoromethyl; R, E, and D are each methyl; Z is —CH(OH)—; X is chlorine; and Y is fluorine.

18. The compound of claim 16 in which M is trifluoromethyl; R, E, and D are each methyl; Z is —CH=CH—; X is chlorine; and Y is fluorine.

19. The compound of claim 16 in which M is trifluoromethyl; R is amino; E is methyl; D is methyl; Z is C=O; X is chlorine; and Y is hydrogen.

20. A compound of claim 15 in which M is trifluoromethyl; R is methyl or amino; E is methyl; D is methoxycarbonyl; Z is $CH_2$, C=O, —CH(OH)—, —$CH_2CH_2$—, —CH=CH—, —(C=O)$CH_2$—, or C=NOCH$_3$; X is bromine or chlorine; and Y is hydrogen or fluorine.

21. The compound of claim 20 in which M is trifluoromethyl; R is methyl; E is methyl; D is methoxycarbonyl; Z is $CH_2$; X is bromine; and Y is hydrogen.

22. The compound of claim 20 in which M is trifluoromethyl; R is methyl; E is methyl; D is methoxycarbonyl; Z is C=O; X is bromine; and Y is hydrogen.

23. A composition comprising an herbicidally effective amount of the compound of claim 1 in admixture with a suitable carrier.

24. A method for controlling undesired plant growth which comprises applying to a locus where control is desired, an herbicidally effective amount of the composition of claim 23.

* * * * *